(12) United States Patent
Boukhny et al.

(10) Patent No.: US 7,945,341 B2
(45) Date of Patent: May 17, 2011

(54) GRAPHICAL USER INTERFACE FOR SELECTING PULSE PARAMETERS IN A PHACOEMULSIFICATION SURGICAL SYSTEM

(75) Inventors: Mikhail Boukhny, Laguna Niguel, CA (US); David Thoe, Aliso Viejo, CA (US)

(73) Assignee: Alcon, Inc., Hunenberg (CH)

(*) Notice: Subject to any disclaimer, the term of this patent is extended or adjusted under 35 U.S.C. 154(b) by 1588 days.

(21) Appl. No.: 11/170,952

(22) Filed: Jun. 30, 2005

(65) Prior Publication Data

US 2006/0235307 A1  Oct. 19, 2006

Related U.S. Application Data

(60) Provisional application No. 60/671,879, filed on Apr. 15, 2005, provisional application No. 60/631,738, filed on Nov. 30, 2004.

(51) Int. Cl.
*G05B 15/00* (2006.01)
*G05B 11/01* (2006.01)
*G01C 19/00* (2006.01)
*G06F 3/00* (2006.01)
*G06F 3/041* (2006.01)
*A61B 17/00* (2006.01)

(52) U.S. Cl. .............. 700/83; 700/14; 702/89; 702/104; 715/784; 715/973; 345/173; 606/1; 606/107; 604/22

(58) Field of Classification Search .............. 700/11–16, 700/83, 87, 90; 702/89, 104; 600/126; 606/1, 606/107; 604/22, 120; 715/700, 784–787, 715/830, 973; 345/23, 24, 173
See application file for complete search history.

(56) References Cited

U.S. PATENT DOCUMENTS

| | | | |
|---|---|---|---|
| 4,812,996 A | 3/1989 | Stubbs | |
| 4,933,843 A | 6/1990 | Scheller et al. | |
| 5,249,121 A | 9/1993 | Baum et al. | |
| 5,371,851 A | 12/1994 | Pieper et al. | |
| 5,455,766 A | 10/1995 | Scheller et al. | |
| 5,554,894 A | 9/1996 | Sepielli | |
| 5,580,347 A | 12/1996 | Reimels | |

(Continued)

FOREIGN PATENT DOCUMENTS

EP  1835872 B1  7/2008
(Continued)

OTHER PUBLICATIONS

European Search Report—Publication No. 1712210.
(Continued)

*Primary Examiner* — Sean P Shechtman
(74) *Attorney, Agent, or Firm* — Jonathan E. Prejean

(57) ABSTRACT

A graphical user interface for use in phacoemulsification surgical systems that allows a user to select different pulse modes by touching portions of the display screen. The user interface includes first and second display elements. One display element includes a representation of the on-time of the pulses, and the other display element includes a representation of the off-time. The representations show how the on-time and off-time change relative to a position of a controller, such as a foot pedal. The representation show a constant time, or that a time increases or decreases as the foot pedal is pressed. To select a pulse mode, a user can scroll through different pulse representations by touching the screen at the display elements. The selected pulse mode can be continuous, pulse, burst and other modes.

47 Claims, 25 Drawing Sheets

U.S. PATENT DOCUMENTS

| | | | |
|---|---|---|---|
| 5,853,367 A | 12/1998 | Chalek et al. | |
| 5,877,957 A * | 3/1999 | Bennett | 700/86 |
| 5,898,434 A | 4/1999 | Small et al. | |
| 5,910,139 A | 6/1999 | Cochran et al. | |
| 5,997,528 A | 12/1999 | Bisch et al. | |
| 6,066,129 A | 5/2000 | Larson | |
| 6,106,512 A | 8/2000 | Cochran et al. | |
| 6,179,829 B1 | 1/2001 | Bisch et al. | |
| 6,251,113 B1 | 6/2001 | Appelbaum | |
| 6,319,220 B1 | 11/2001 | Bylsma | |
| 6,366,300 B1 | 4/2002 | Ohara | |
| 6,428,508 B1 | 8/2002 | Ross | |
| 6,442,440 B1 | 8/2002 | Miller | |
| 6,507,796 B2 | 1/2003 | Alexander | |
| 6,512,530 B1 | 1/2003 | Rzepkowski et al. | |
| 6,583,796 B2 | 6/2003 | Jamar et al. | |
| 6,628,996 B1 * | 9/2003 | Sezaki et al. | 700/83 |
| 6,659,998 B2 | 12/2003 | DeHough et al. | |
| 6,671,535 B1 | 12/2003 | McNichols et al. | |
| 6,707,474 B1 | 3/2004 | Beck et al. | |
| 6,783,523 B2 | 8/2004 | Qin et al. | |
| 7,077,820 B1 | 7/2006 | Kadziauskas et al. | |
| 7,225,405 B1 | 5/2007 | Barrus et al. | |
| 2002/0045887 A1 | 4/2002 | DeHoogh | |
| 2002/0054144 A1 | 5/2002 | Morris-Yates | |
| 2003/0073980 A1 | 4/2003 | Finlay et al. | |
| 2003/0137535 A1 | 7/2003 | Heo | |
| 2003/0195462 A1 * | 10/2003 | Mann et al. | 604/67 |
| 2004/0024384 A1 | 2/2004 | Novak | |
| 2004/0092922 A1 | 5/2004 | Kadziauskas et al. | |
| 2005/0080348 A1 | 4/2005 | Stahmann et al. | |
| 2006/0074405 A1 | 4/2006 | Malackowski et al. | |
| 2006/0114175 A1 | 6/2006 | Boukhny | |
| 2006/0235307 A1 | 10/2006 | Boukhny et al. | |
| 2006/0236242 A1 | 10/2006 | Boukhny et al. | |
| 2006/0248477 A1 | 11/2006 | Boukhny et al. | |
| 2007/0056596 A1 | 3/2007 | Fanney et al. | |
| 2007/0073214 A1 | 3/2007 | Dacquay et al. | |
| 2007/0078379 A1 | 4/2007 | Boukhny et al. | |
| 2009/0049397 A1 | 2/2009 | Boukhny | |

FOREIGN PATENT DOCUMENTS

| | | |
|---|---|---|
| WO | WO 96/13216 A1 | 5/1996 |
| WO | WO 98/08442 | 3/1998 |
| WO | WO 98/25556 A1 | 6/1998 |
| WO | WO 02/32354 | 4/2002 |

OTHER PUBLICATIONS

European Search Report—Publication No. 1712211.
European Search Report—Publication No. 1712209.
European Search Report for Application No. 07111481.3, filed Apr. 13, 2006, Published Sep. 26, 2007, Publication No. 1837002, 2 pages.
International Search Report for PCT/US2005/043,188, Publication No. WO2006060423, 3 pages.
Non-Final Office Action, U.S. Appl. No. 11/193,159, filed Jul. 29, 2005, 36 pages.

* cited by examiner

"PRIOR ART"

"PRIOR ART"

"PRIOR ART"

"PRIOR ART"

610
 640
 620
 620
 600
 630

GRAPHICAL USER INTERFACE FOR SELECTING PULSE PARAMETERS IN A PHACOEMULSIFICATION SURGICAL SYSTEM

CROSS REFERENCE TO RELATED APPLICATION

This application claims priority under 35 U.S.C. §119 to U.S. Provisional Patent Application No. 60/671,879, filed Apr. 15, 2005, and to U.S. Provisional Patent Application No. 60/631,738 filed Nov. 30, 2004, the entire disclosure of which is incorporated herein by reference.

TECHNICAL FIELD OF THE INVENTION

The invention relates generally to graphical user interfaces for surgical systems, and, more particularly, to graphical user interfaces for phacoemulsification surgical systems that include representations of the functions or behavior of pulse parameters and characteristics, such as on-time and off-time, which can be adjusted by touching the display screen.

BACKGROUND OF THE INVENTION

Modern surgical systems, and in particular, modern ophthalmic surgical systems, are designed to monitor and display multiple parameters of a surgical device or instrument that is connected to the surgical system and controlled by the surgeon through the use of a foot pedal. Such systems can be complex given the multiple parameters that must be displayed and controlled by a surgeon, particularly during a surgical procedure.

Certain known phacoemulsification systems allow for application of ultrasound energy at a fixed level. For example, the foot pedal acts as an on/off switch to activate and deactivate ultrasound energy that is at a particular power level. When the foot pedal is pressed, the device is activated and the power level is constant and without interruptions, that is "continuous." Continuous power is approximately proportional to the amount of voltage applied to the piezoelectric crystals in the phacoemulsification handpiece.

"Continuous" power systems were improved by the introduction of "linear" mode, which allows a surgeon to control power in a variable manner. A surgeon controls power based on the foot pedal position so that the power is proportional to or linear with respect to the displacement of the foot pedal. Thus, more power is provided as the surgeon presses the foot pedal, and less power is provided as the foot pedal is released. Further improvements involved the introduction of "pulse" mode. In "pulse" mode, phacoemulsification energy is provided in periodic pulses at a constant duty cycle. The surgeon increases or decreases the amount of power by pressing or releasing the foot pedal, which increases or decreases the amplitude of the fixed-width pulses. Further enhancements involved the introduction of "burst" mode. In "burst" mode, power is provided through a series of periodic, fixed width, constant amplitude pulses. Each pulse is followed by an "off" time. The off-time is varied by the surgeon by pressing and releasing the foot pedal.

In order to accommodate continuous, "linear," "pulse" and "burst" mode and their operating parameters, known user interfaces of phacoemulsification systems typically include several human actionable controllers and fields or elements that occupy particular positions on a display screen. Some known user interfaces include buttons, arrows, switches, bars and/or knobs for setting desired numeric values of operating characteristics of the surgical system. Certain parameters are fixed or have a constant value regardless of the foot pedal position, whereas other parameters vary, e.g., vary linearly, with the foot pedal. The interface is manipulated by a surgeon to provide control signals to the surgical instruments which, in turn, control the modes or types of pulses that are generated.

FIGS. 1 and 2 illustrate one known interface for a phacoemulsification surgical system. A surgeon manually selects the power mode from a selection bar or menu 10. In this interface, the menu 10 includes "Ultrasound Continuous," "Ultrasound Pulse," and "Ultrasound Burst" menu bars 12, 14 and 16, respectively. In the example illustrated in FIGS. 1 and 2, the continuous power menu bar 12 is selected from the menu 10. The power limit is represented in a field 20. The maximum amount of continuous power or the power limit is adjusted using up/down arrows 24. In this example, the continuous power limit is selected to be "35" or 35% of the maximum allowed power. The continuous power varies linearly, as shown by the line 26 in the background of the power limit window 20 up to a maximum value of 35%. The current power level is provided in a field 28. In the illustrated example, the current power is "0" or 0% in this example since the screen represents current power when the foot pedal is released. Pressing the foot pedal results in power increasing linearly from 0% to 35%. When the surgeon wants to change from "continuous" mode to another mode, the surgeon selects the "ultrasound continuous" bar 12 so that the menu 10 of available pulse modes is displayed. The surgeon can then select another mode from the menu 10.

Application of periodic ultrasound pulses can be described based on power, the duration of the pulses, the "On" or active time, and the duration of "Off" time or the duration between pulses. Alternatively, pulses can be specified using pulse rate and duty cycle. Pulse rate is the number of pulses contained in unit time. Duty cycle is the portion of the ultrasound cycle when the ultrasound is active. In other words, duty cycle is the ratio of On/(On+Off).

FIG. 3 illustrates "Ultrasound Pulse" menu bar 14 being selected from the menu 10. A surgeon manually selects a maximum power level of 35%, which varies linearly as the foot pedal is pressed and released. In addition, the interface includes a field 30 for the pulse rate or pulses per second (pps) and a field 40 for the "on-time" (% Time on). The number of pulses per second (pps) and the on-time, however, do not vary with movement of the foot pedal. Rather, the pps is fixed at 14 pps using arrows 34, and the on-time is fixed at 45% using arrows 44. Thus, the pps and on-time values do not change when the foot pedal is displaced and must be manually adjusted by the surgeon using arrows 34 and 44. Power increases linearly from 0-35% as the foot pedal is pressed, and is delivered at a fixed rate of 14 pulses per second at a fixed 45% duty cycle.

Referring to FIGS. 2 and 4, when "Ultrasound Burst" mode is selected from the menu 10, the same limit and power field 28 and limit field 20 are provided. The power varies linearly with the foot pedal, as discussed above. Rather than pps and on time fields 30 and 40 (as shown in FIG. 3), the interface displays a field 50 for on-time or On (ms) and a field 60 for off time or Off (ms) when in "burst" mode. The On (ms) value is fixed and does not change when the foot pedal is moved. The on-time (ms) is shown fixed at 70 ms and can be adjusted using arrows 54. The Off time decreases from a value to 0 ms with the foot pedal displacement. In this "burst" mode, the power increases from 0-40% as the foot pedal is depressed by changing the "off-time", and the duration of each pulse remains a constant 70 ms throughout displacement of the foot pedal.

While known interfaces have been successfully used to perform phacoemulsification procedures in the past, they can be improved. Particularly, the visual and functional aspects of interfaces can be enhanced so that surgeons can select and control different pulse modes and can easily switch between different modes. User interfaces should include additional controllable display elements that allow different modes and their parameters to be quickly and easily adjusted. These improvements should be made without unduly complicating the user interface and how it functions. Further, interfaces should be capable of effectively representing various operating parameters of various ultrasound driving modes, including continuous, linear, pulse, burst, and new modes, which can be combinations and modifications of known modes. Being able to quickly adjust pulse parameters in an understandable manner also simplifies setting up the equipment, reduces operating costs and improves safety.

BRIEF SUMMARY OF THE INVENTION

According to one embodiment of the invention, a user interface for a phacoemulsification surgical system that generates pulses having an on-time and an off-time and that are adjusted in response to a controller based on settings displayed on a display screen includes a first display element and a second display element. The first display element includes a representation of the on-time relative to a position of the controller. A current on-time representation is changed to a different on-time representation in response to touching the display screen at the first display element. The second display element includes a representation of the off-time relative to a position of the controller. A current off-time representation is changed to a different off-time representation in response to touching the display screen at the second display element. The on-time and off-time representations are selected to generate pulses in a desired mode.

According to an alternative embodiment of the invention, a user interface for a phacoemulsification surgical system that generates pulses having an on-time and an off-time and that are adjusted in response to a controller based on settings displayed on a display screen includes first and second display elements. The first display element includes a representation of the on-time relative to a position of the foot pedal. At least three on-time representations are sequentially displayed in the first display element by touching the display screen at the first display element. This allows a user to scroll through the on-time representations. The on-time representation that is displayed in the first display element is the selected on-time representation. A second display element includes a representation of the off-time relative to a position of the foot pedal. At least three off-time representations are sequentially displayed in the second display element by touching the display screen at the second display element. This allows a user to scroll through the off-time representations. The off-time representation that is displayed in the second display element is the selected off-time representation. The on-time and off-time representations are selected to generate pulses in a desired mode.

In accordance with yet a further alternative embodiment of the invention, a user interface for a phacoemulsification surgical system that generates pulses having an on-time and an off-time that is adjusted in response to a foot pedal and based on settings in a user interface displayed on a display screen includes a first display element, a second display element, an on-time value and an off-time value. The first display element includes a linear representation of the on-time of pulses that are generated by the phacoemulsification system relative to a position of the foot pedal. The on-time representation is a decreasing linear or non-linear representation, a horizontal representation, or an increasing linear or non-linear representation. At least three on-time representations are sequentially displayed in the first display element by touching the display screen at the first display element. This allows a user to scroll through the on-time representations. The on-time representation that is displayed in the first display element is the selected on-time representation. An on-time value displayed in the first display element indicates a value of the on-time. According to one embodiment, the on-time representation is displayed in the background relative to the on-time value. The second display element includes a representation of the off-time of pulses generated by the phacoemulsification system relative to a position of the foot pedal. The linear off-time representation is a decreasing linear or non-linear representation, a horizontal representation, or an increasing linear or non-linear representation. At least three off-time representations are sequentially displayed in the second display element by touching the display screen at the second display element. This allows a user to scroll through the off-time representations. The off-time representation that is displayed in the second display element is the selected off-time representation. The off-time value display indicates a value of the off-time of the pulses and appears within the second display element. According to one embodiment, the off-time representation is displayed in the background relative to the off-time value. The on-time and off-time representations are selected to generate pulses in a desired mode.

In various embodiments, a user may scroll through different numbers of on-time and off-time representations, and current representations can be replaced with different representations each time the display screen is touched at a display element. The representations can be linear, non-linear, increasing, decreasing, constant or horizontal, and combinations thereof. Non-linear representations can be exponentials and polynomials. The system can be configured so that the on-time and/or off-time parameter is adjusted in accordance with the function displayed in the corresponding display element in response to a controller, e.g., a foot pedal. Off-time and on-time representations can also be changed and selected using a menu.

In various embodiments, the system generates pulse mode pulses by setting the user interface so that the on-time representation in the first display element is a horizontal linear representation. This represents the on-time remaining substantially constant. The user interface is also set so that the off-time representation in the second display element is a horizontal linear representation, which also represents the off-time remaining substantially constant. Burst mode pulses can be generated by setting the user interface so that the on-time representation in the first display element is a horizontal linear representation, representing that the on-time remaining substantially constant, and the off-time representation in the second display element is a decreasing linear representation, representing that the off-time decreasing linearly in response to movement of the controller.

BRIEF DESCRIPTION OF THE SEVERAL VIEWS OF THE DRAWINGS

A more complete understanding of embodiments and the advantages thereof may be acquired by referring to the following description, taken in conjunction with the accompanying drawings, in which like reference numbers indicate like features and wherein.

DETAILED DESCRIPTION OF THE INVENTION

Figure 1:
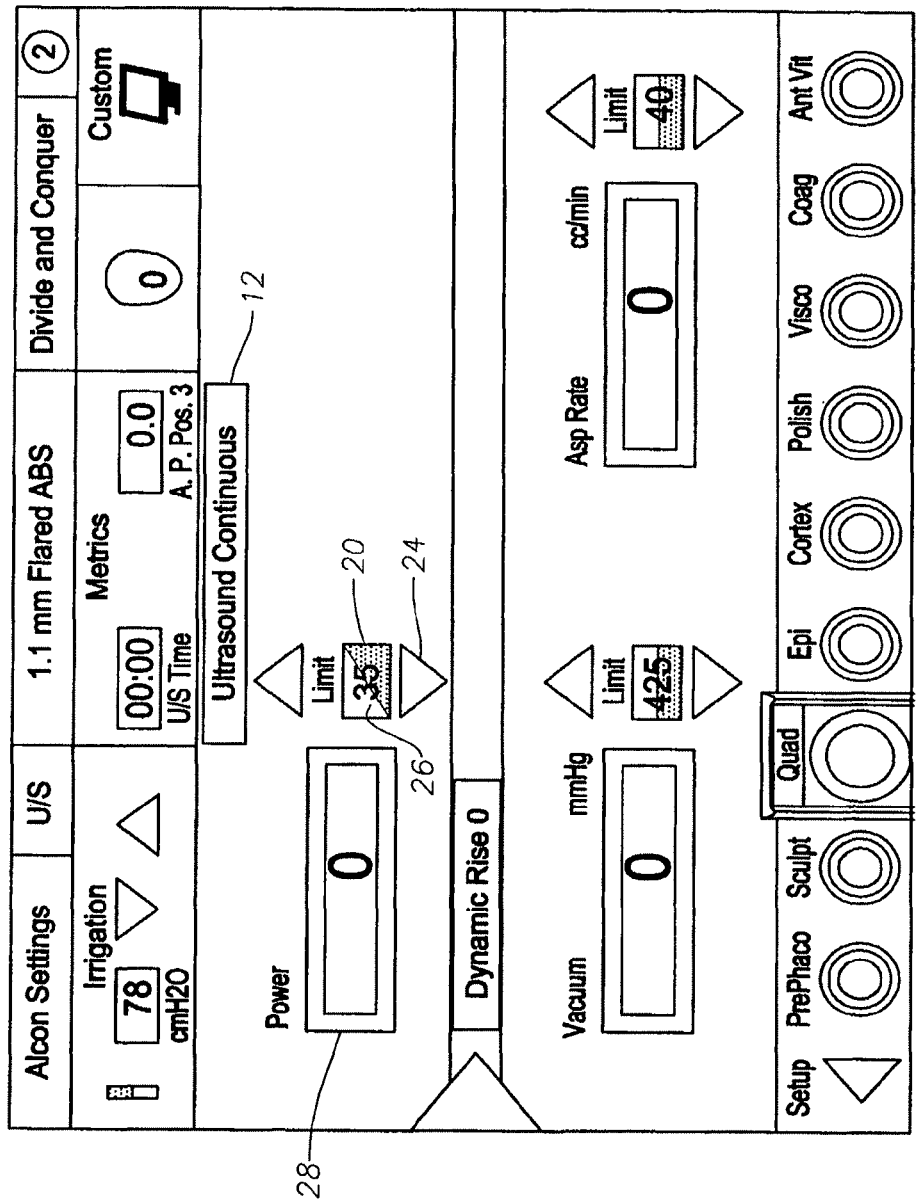
FIG. 1 illustrates a known graphical user interface for use with a phacoemulsification surgical system in "continuous" mode.
Figure 2:
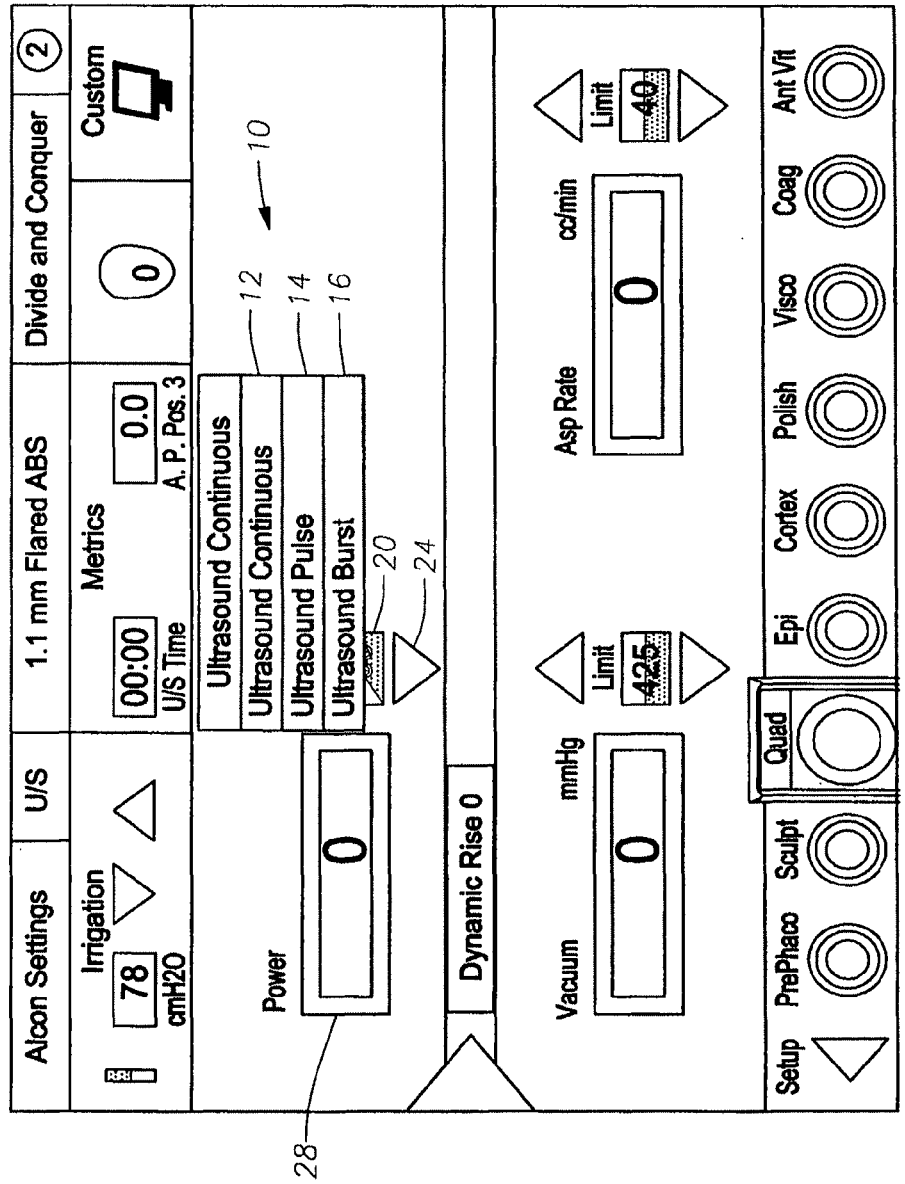
FIG. 2 illustrates the interface shown in FIG. 1 after the "continuous" mode menu bar is selected to generate a drop down menu of available pulse modes.

In the following description, reference is made to the accompanying drawings which form a part hereof, and which show by way of illustration specific embodiments in which the invention may be practiced. It is to be understood that changes may be made without departing from the scope of invention.

Embodiments of the invention are directed to a graphical user interface that provides improved control over the ultrasound driving or pulse modes that are generated by a phacoemulsification surgical system and improved control over the parameters of the different pulse modes. Embodiments provide display elements that can be quickly and easily selected and adjusted by a surgeon to select different modes, while allowing various pulse parameters to be adjusted to customize the various modes. The pulse modes that can be selected include "Continuous," "Pulse" and "Burst" modes and, in addition, hybrid or combination modes that were not previously readily available for use in phacoemulsification systems. Representations of parameters, characteristics and the functions of pulses are displayed in display elements. The representations can be changed by touching a display screen at a particular display element to generate a menu from which a representation of a pulse characteristic, such as the on-time and the off-time, can be selected by the user. Alternatively, a user can scroll through different representations of the characteristics or function of the on-time and the off-time of the pulses. The representation that is selected represents the function or behavior of the pulse characteristic, e.g., whether and how the on-time and the off-time vary in response to displacement of a controller, such as a foot pedal, and the types and characteristics of pulses that are generated by the phacoemulsification system. A separate window can be generated in response to touching the display screen to adjust the representation and/or values.

Embodiments of the invention provide improvements over known interfaces by allowing on-time, off-time and other pulse parameter representations to be adjusted so that they increase linearly, increase non-linearly, decrease linearly, decrease non-linearly, and remain substantially constant relative to displacement of a foot pedal. These settings determine whether the on-time and/or off-time decrease or increase linearly or non-linearly or remain constant. Different pulse modes can be generated by selecting the manner in which the on-time and the off-time vary (or not vary). For example, nine different pulse modes can be selected when the on-time and the off-time each can increase, decrease or remain constant in response to movement of the foot pedal. The power limit, the on-time and the off-time, can be adjusted using up/down arrows and other suitable adjustment mechanisms. Persons skilled in the art will appreciate that embodiments of the invention can be utilized with other surgical equipment including, but not limited to, neurosurgery equipment, where control of various instruments is also performed with a remote foot pedal. For purposes of explanation, not limitation, this specification describes embodiments related to phacoemulsification procedures and their associated operating parameters.

Figure 5:
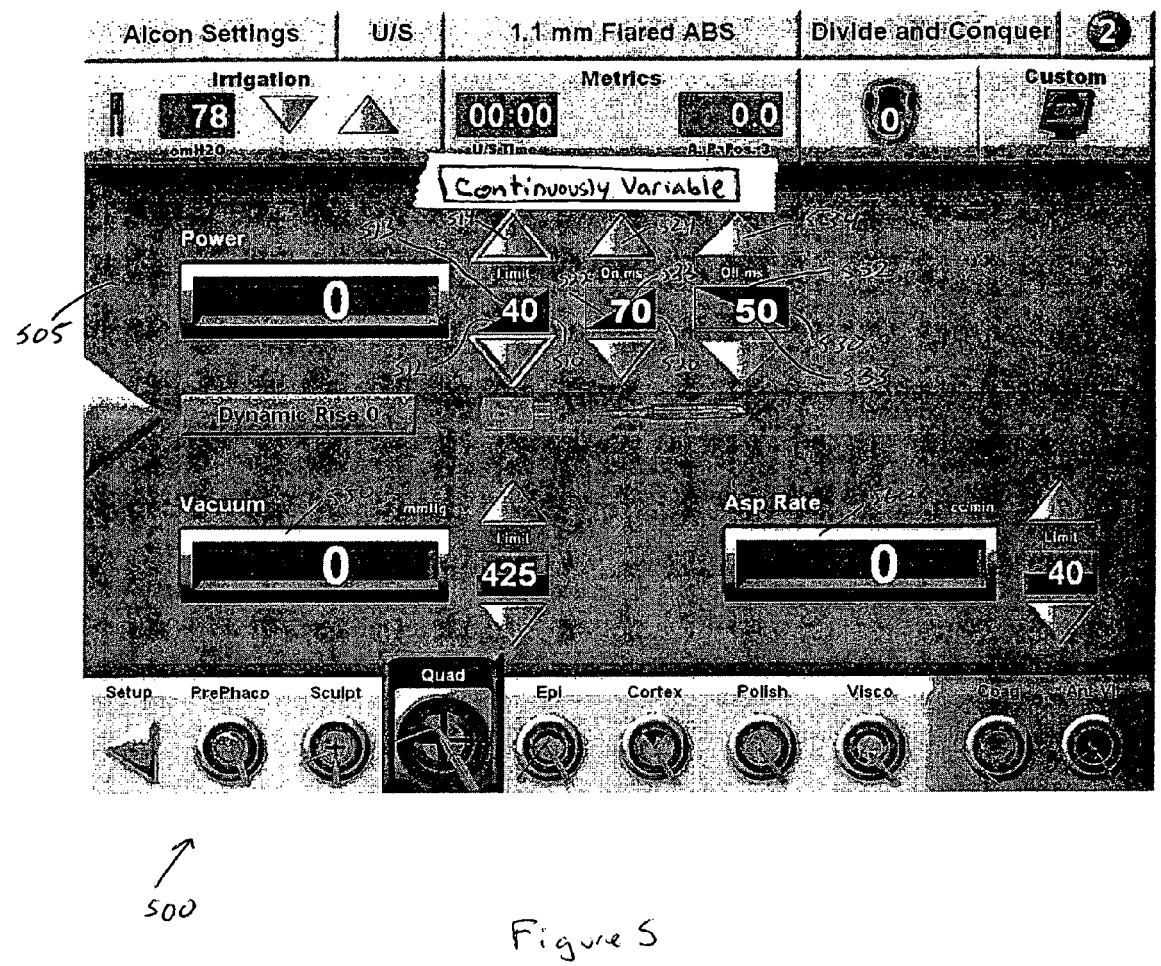
FIG. 5 illustrates a graphical user interface according to one embodiment of the invention that includes representations of the functions of pulse on-time and off-time.

Referring to FIG. 5, a user interface 500 for a phacoemulsification surgical system according to one embodiment is displayed on a display screen 505 of the system. The interface 500 includes a power display element 510, an on-time display element 520, and an off-time display element 530.

The current power level, as controlled by the foot pedal, is shown in a current power display element 540. In the illustrated embodiment, the display elements 510, 520 and 530 are rectangle-shaped display elements. Indeed, other shapes besides rectangular shapes can be utilized, and rectangle-shaped display elements are provided for purposes of illustration, not limitation. The interface 500 also includes other display elements and adjustments for other phacoemulsification surgical parameters, such as aspiration flow rate (Asp Rate) 550 and vacuum limit pressure (Vacuum) 560, as known in the art. Operation of these other display elements 550 and 560 is not discussed further in this specification. Pressing and releasing the foot pedal controls the operation of the surgical devices according to the corresponding operating parameters and parameter values that are represented in the interface 500 and programmed in the system.

The power display element 510 includes a representation 512 of the behavior or function of power relative to a position of the foot pedal, the on-time display element 520 includes a representation 522 of the behavior or function of the on-time of the pulses relative to a position of the foot pedal, and the off-time display element 530 includes a representation 532 of the behavior or function of the off-time of the pulses relative to a position of the foot pedal. In one exemplary surgical system, the parameter values change when the foot pedal moves, and the parameter values reflect the actual parameter values. When the foot pedal is not depressed, the values that are displayed are the limits of the values that are achieved when the foot pedal fully depressed. Persons skilled in the art will appreciate that other conventions can be used and the described convention is an exemplary convention.

The graphic representations can be easily and quickly selected and adjusted by a surgeon before and during surgery. The display elements 510, 520 and 530 also includes respective power, on-time and off-time limits or values 513, 523 and 533. Although embodiments are described with reference to "Off" or off-time and "On" of on-time, persons skilled in the art will appreciate that other ultrasound parameters, such as pps and duty cycle, and non-ultrasound parameters can be represented in a user interface. For purposes of explanation, not limitation, this specification refers to on-time and off-time parameters. Further, persons skilled in the art will appreciate that different combinations of parameters can be used to represent different types of pulses. For purposes of explanation, this specification refers to on-time and off-time.

Figure 6:
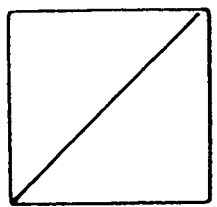
FIG. 6 illustrates exemplary linear and non-linear representations of pulse characteristics or parameters relative to a position of a foot pedal according to one embodiment.
Figure 6:
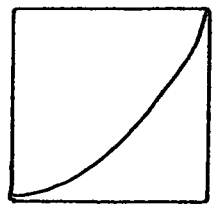
Figure 6:
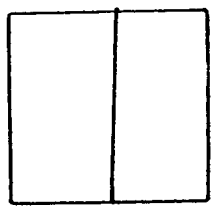
Figure 6:
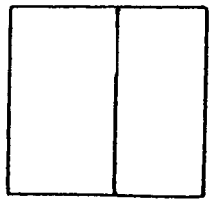
Figure 6:
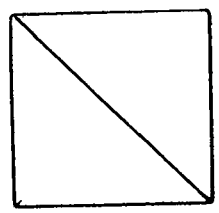
Figure 6:
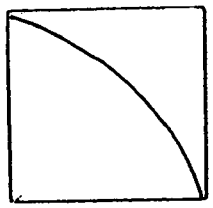

Referring to FIG. 6, a representation of a pulse characteristic can have various shapes depending on the desired relationship or function between the pulse parameter and the position of the foot pedal. A representation of a characteristic or parameter of a pulse can be linear or non-linear, to represent a linear or non-linear function of power, on-time and/or off-time. A linear representation can be an increasing linear representation 600, a horizontal or constant linear representation 610, and a decreasing linear representation 620. A non-linear representation can be an increasing non-liner representation 630 and a decreasing non-linear representation 640.

Figure 7:
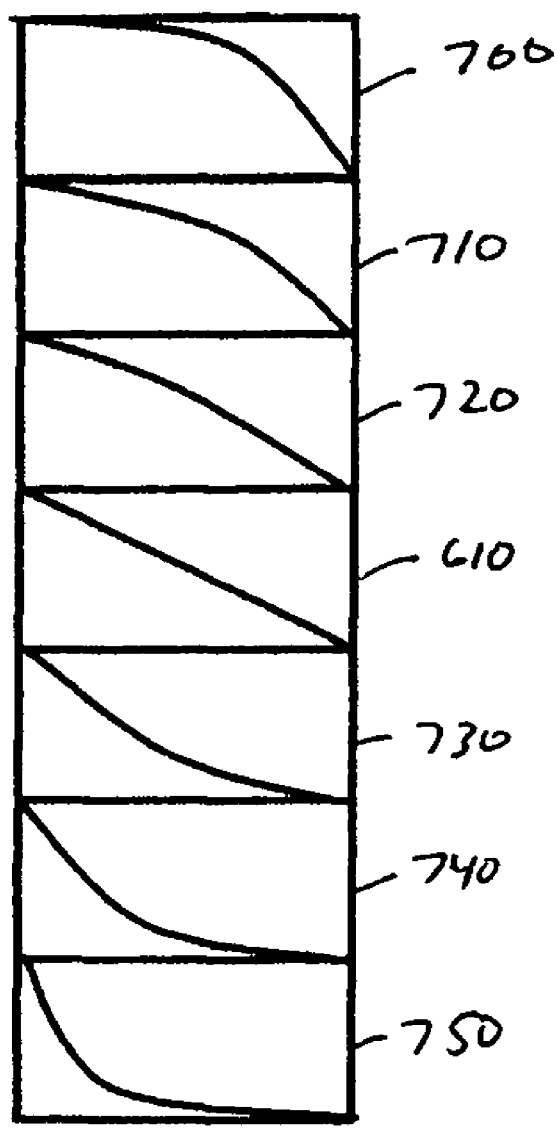
FIG. 7 illustrates exemplary non-linear representations of on-time and off-time that decrease when the foot pedal is pressed.
Figure 8:
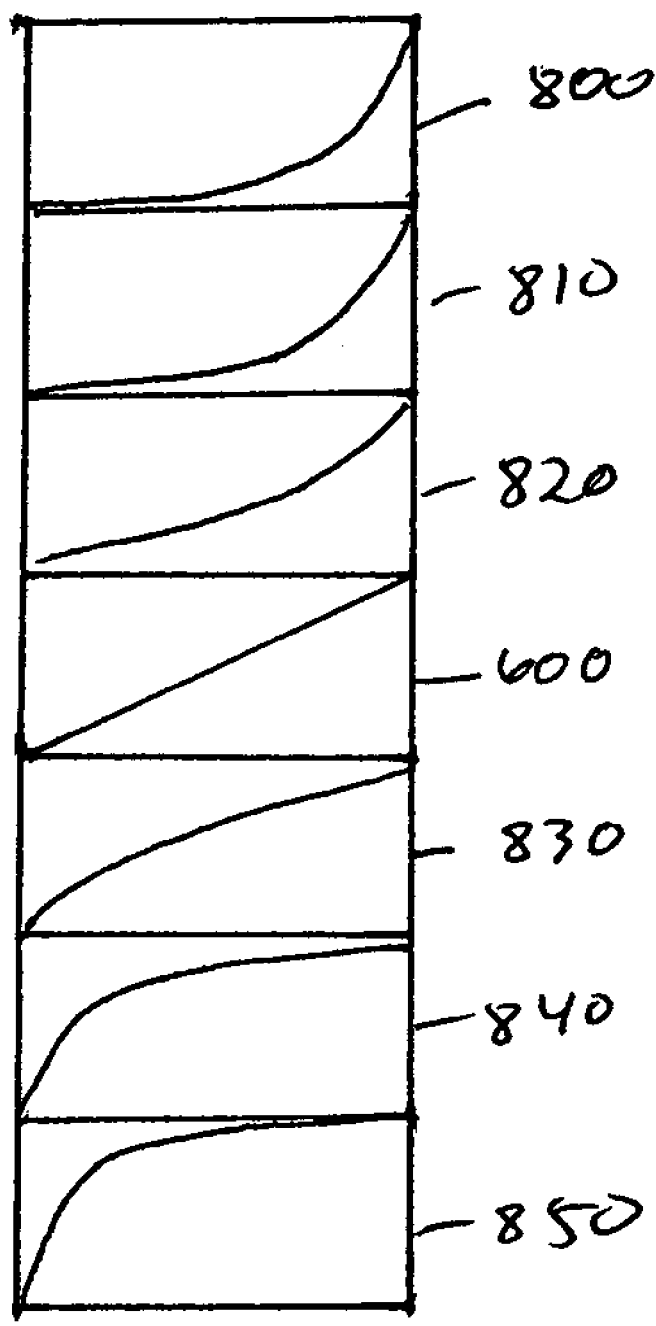
FIG. 8 illustrates exemplary non-linear representations of on-time and off-time that increase when the foot pedal is pressed.

FIG. 7 illustrates exemplary non-linear representations. Non-linear representations 700-750 decrease non-linearly in different manners. Exemplary non-linear representations include exponential and polynomial representations so that the power, on-time and/or off-time varies exponentially or in accordance with a polynomial with movement of the foot pedal. Representations 700-720 and corresponding functions of the power, on-time and/or off-time decrease less rapidly when the foot pedal is initially depressed, and decrease more rapidly as the foot pedal is depressed further. Representations 730-750 and corresponding functions of the power, on-time and/or off-time decrease more rapidly when the foot pedal is initially depressed, and decrease more slowly as the foot pedal is depressed further. FIG. 8 illustrates similar relationships with increasing representations of the behavior or functions of a power, on-time and/or off-time.

For purposes of explanation and illustration, not limitation, this specification refers to linear representations, e.g., increasing linear, constant, and decreasing linear representations and related linear functions of power, on-time and/or off-time. Persons skilled in the art will appreciate that the power, on-time and off-time can be controlled with linear representations, non-linear representations and combinations thereof. Persons skilled in the art will also appreciate that a linear representation may represent a characteristic of a pulse that is substantially linear and that includes some non-linear components in actual practice. For example, the relationship between the actual power and the position of the foot pedal may not be exactly linear due to mapping the foot pedal position to the amount of power that is generated. Thus, there may be some deviations from a truly "linear" representation in practice due to mapping and other factors.

In the embodiments shown in FIG. 6, an increasing linear representation 600 extends from a bottom left corner to a top right corner of a display element to illustrate that the parameter being represented increases linearly as the foot pedal is pressed and decreases linearly as the foot pedal is released. A horizontal or constant linear representation 620 extends between opposite sides of a display element and illustrates that the parameter being represented remains substantially constant at various foot pedal positions. A decreasing linear representation 630 extends from a bottom left corner to a top right corner of a display element and illustrates that the parameter being represented decreases linearly as the foot pedal is pressed and increases linearly as the foot pedal is released. In alternative embodiments, increasing and decreasing linear representations 600 and 610 and corresponding functions of the pulse parameter may extend between a side and a corner of a display element or two sides of a display element, while still showing an increasing or decreasing relationship. This may represent, for example, that the starting value of the pulse parameter, such as the on-time and the off-time, is a non-zero value.

Referring again to FIG. 5, the power limit display element 510 includes a power limit or value 513, the on-time display element 520 includes an on-time limit or value 523 and the off-time display element includes an off-time limit or value 533. The limits are adjusted using respective up/down arrows 514, 524 and 534 or other suitable adjustment mechanisms, such as slide bars (not shown in FIG. 5). This specification refers to up/down arrows for purposes of illustration, not limitation. Initial power, on-time and off-time values, whether minimum or maximum values, can be set or programmed as necessary. For example, the system can be configured so that the minimum power value is 0% or another desired value when the foot pedal is in its home position, e.g., when the foot pedal is released. As a further example, the initial on-time or, alternatively, the minimum on-time, can be 0 ms or a non-zero value. Similarly, the initial off-time or, alternatively, the minimum off-time, can be 0 ms or a non-zero value. Initial values or, alternatively, minimum values, can set using another interface screen or programming the values into the system. Maximum power, on-time and off-time can also be set or programmed as appropriate.

For example, if the on-time is an increasing function (e.g., increasing linear function), then the on-time limit 523 represents the maximum on-time that can be achieved when the foot pedal is fully depressed. The minimum on-time can be zero or another selected value, e.g., 20% of the maximum value. The minimum on-time can be determined using a formula function or other techniques. As a further example, if the on-time function is a decreasing function, then the on-time limit 523 represents the minimum on-time value that can be achieved when the foot pedal is fully depressed. The maximum on-time can be selected as appropriate. Similar controls apply to the power and off-time limits. The following examples illustrate these relationships.

If the maximum value 523 of the on-time is 70 ms and the on-time representation 522 increases linearly, then the on-time increases linearly from zero or a minimum value (e.g., 20% of 70 ms) to 70 ms in a linear manner as the foot pedal is pressed. The minimum on-time or starting point can be set or programmed as needed. As a further example, if the on-time representation 522 decreases linearly, then the on-time decreases from a maximum value to a minimum value of 70 ms in a linear manner as the foot pedal is pressed. The maximum on-time or starting point can be set or programmed as needed.

Similarly, if the off-time limit 533 is 70 ms and the off-time representation 532 increases linearly, then the off-time increases from a minimum value to 70 ms as the foot pedal is pressed. As a further example, if the off-time decreases linearly, then the off-time decreases from a maximum value to a minimum value of 70 ms in a linear manner as the foot pedal is pressed.

If the maximum value of the off-time is 50 ms, and the off-time representation is horizontal, then the off-time remains substantially constant at 50 ms at different foot level positions. If the maximum value of the on-time is 50 ms, and the on-time representation is horizontal, then the on-time remains substantially constant at 50 ms at different foot level positions.

Thus, the limit values 513, 523 and 533 within each of the power, on-time and off-time display elements 510, 520 and 530 represent a maximum or minimum limit of each parameter when the foot pedal is fully depressed depending on whether the parameter increases or decreases when the foot pedal is pressed. The limit value is a maximum value when the parameter increases when the foot pedal is pressed, and is a minimum value when the parameter decreases when the foot pedal is pressed.

In the illustrated embodiment, the values are superimposed over their respective representations. In other words, the representation appears in the background of a display element. For example, the value 514 is superimposed over the power representation 512, the value 524 is superimposed over the on-time representation 522 and the value 534 is superimposed over the off-time representation 532. In alternative embodiments, the representations can also be superimposed over the values depending on display preferences.

Figure 9:
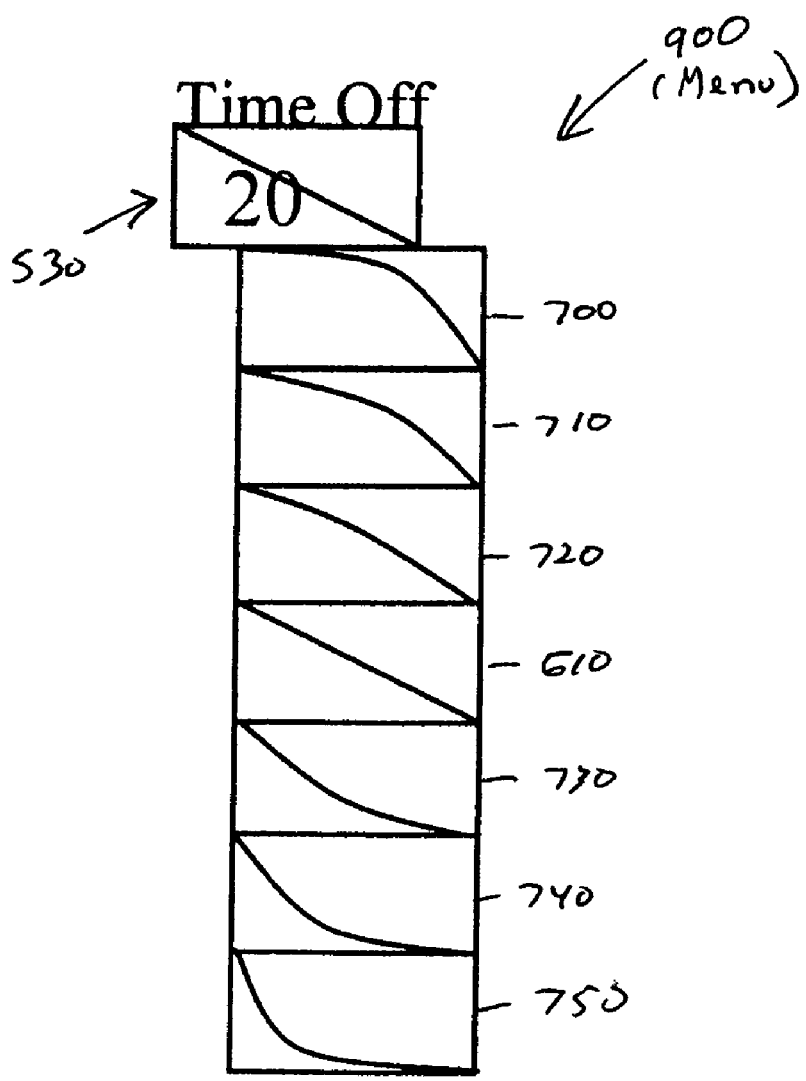
FIG. 9 illustrates a menu that includes representations of off-time according to one embodiment in which off-time decreases when the foot pedal is pressed.

A surgeon can select and switch representations and the manner in which the power, on-time and off-time function in different manners. Referring to FIG. 9, according to one embodiment, the surgeon can touch the display screen at a display element so that a menu 900 of different representations is displayed as a drop-down list. The surgeon can then select a new representation or function of the power, on-time and/or off-time from the menu 900. For example, referring to FIGS. 5 and 9, a surgeon can touch the display screen 505 at the off-time display element 530. As a result, a menu 900 of decreasing representations is displayed, and the surgeon can then select one of the representations from the menu 900. The selected representation represents how the pulse characteristic functions. The menu 900 can include different numbers of decreasing, increasing and constant or horizontal representations. FIG. 9 illustrates a menu 900 having decreasing representations for purposes of illustration, not limitation. Each of the power limit, on-time and off-time representations can be adjusted using a menu 900.

Figure 10:
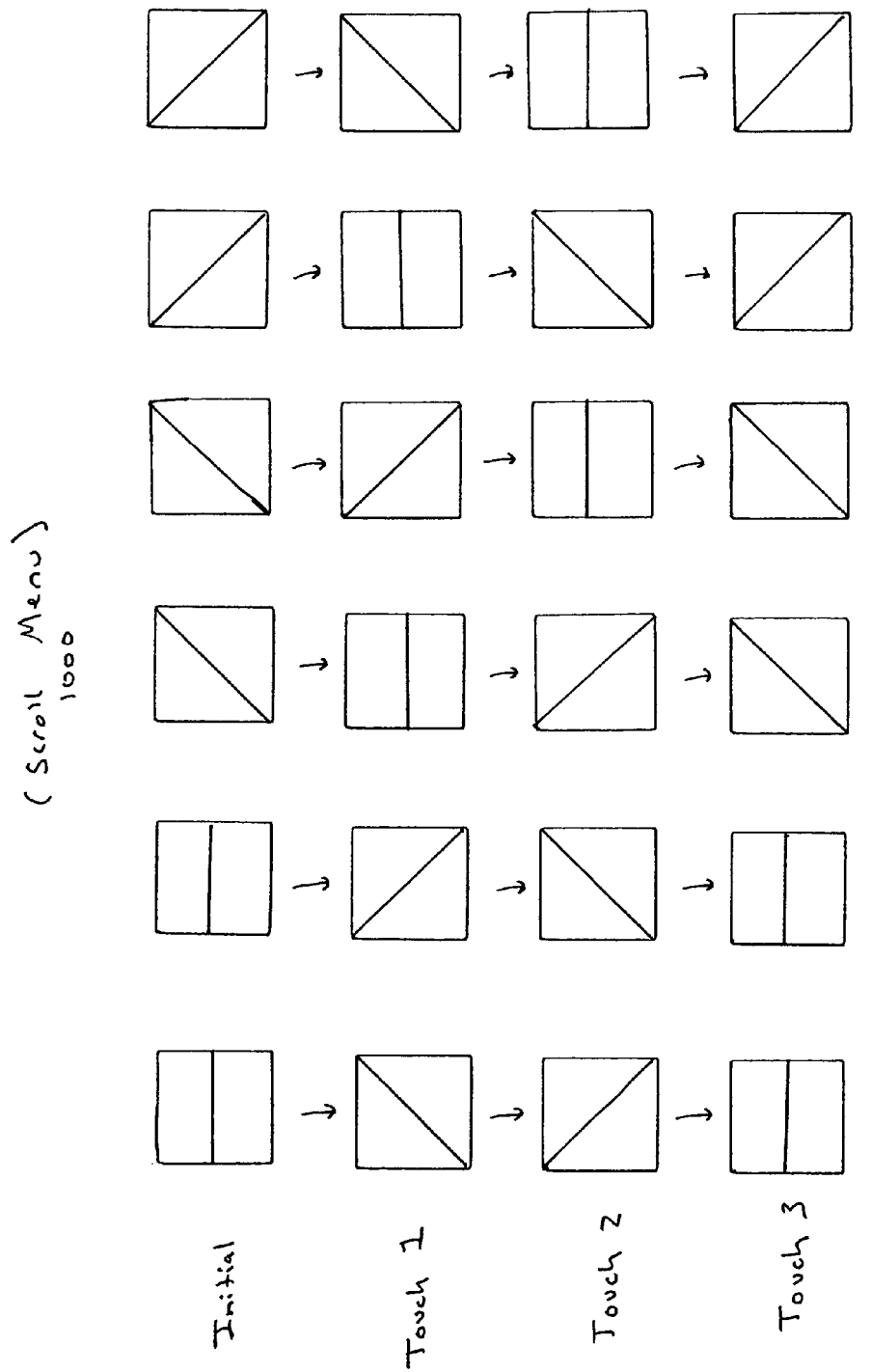
FIG. 10 illustrates exemplary sequences of displaying horizontal, increasing and decreasing on-time and off-time representations according to one embodiment in which a user can scroll through different representations.

Referring to FIG. 10, according to another embodiment, a surgeon can touch the display screen 500 at a display element to change the representation of the pulse characteristic to the desired representation using a scroll menu 1000. Thus, different representations are shown to the surgeon individually rather than shown as a group or menu 900, as shown in FIG. 9. In this embodiment, each time the surgeon touches the display screen 505 at a particular display element, the representation of that pulse parameter changes to a new representation. In other words, the surgeon can scroll through different representations of pulse characteristics by touching the display screen 505 at the corresponding display element.

The representations in a scroll menu can appear to the surgeon in different orders. For example, if the initial representation is a horizontal representation, a first touch (Touch 1) of a display element can change the horizontal representation to a linear increasing representation. The next touch (Touch 2) can change the linear increasing representation to a linear decreasing representation. The next touch (Touch 3) can change the linear increasing representation to the horizontal representation. Each of the power limit, on-time and off-time representations can be adjusted in this manner. FIG. 10 illustrates other sequences in which representations may be displayed to a surgeon in response to the surgeon touching the display screen at a display element. Further, alternative embodiments can include other numbers of representations and thus, other sequences of representations that are displayed.

Different ultrasound driving or pulse modes can be generated by the phacoemulsification system by selecting representations of the function or behavior of the power, on-time and off-time, using a menu shown in FIG. 9 or a scrolling menu shown in FIG. 10.

Figure 11:
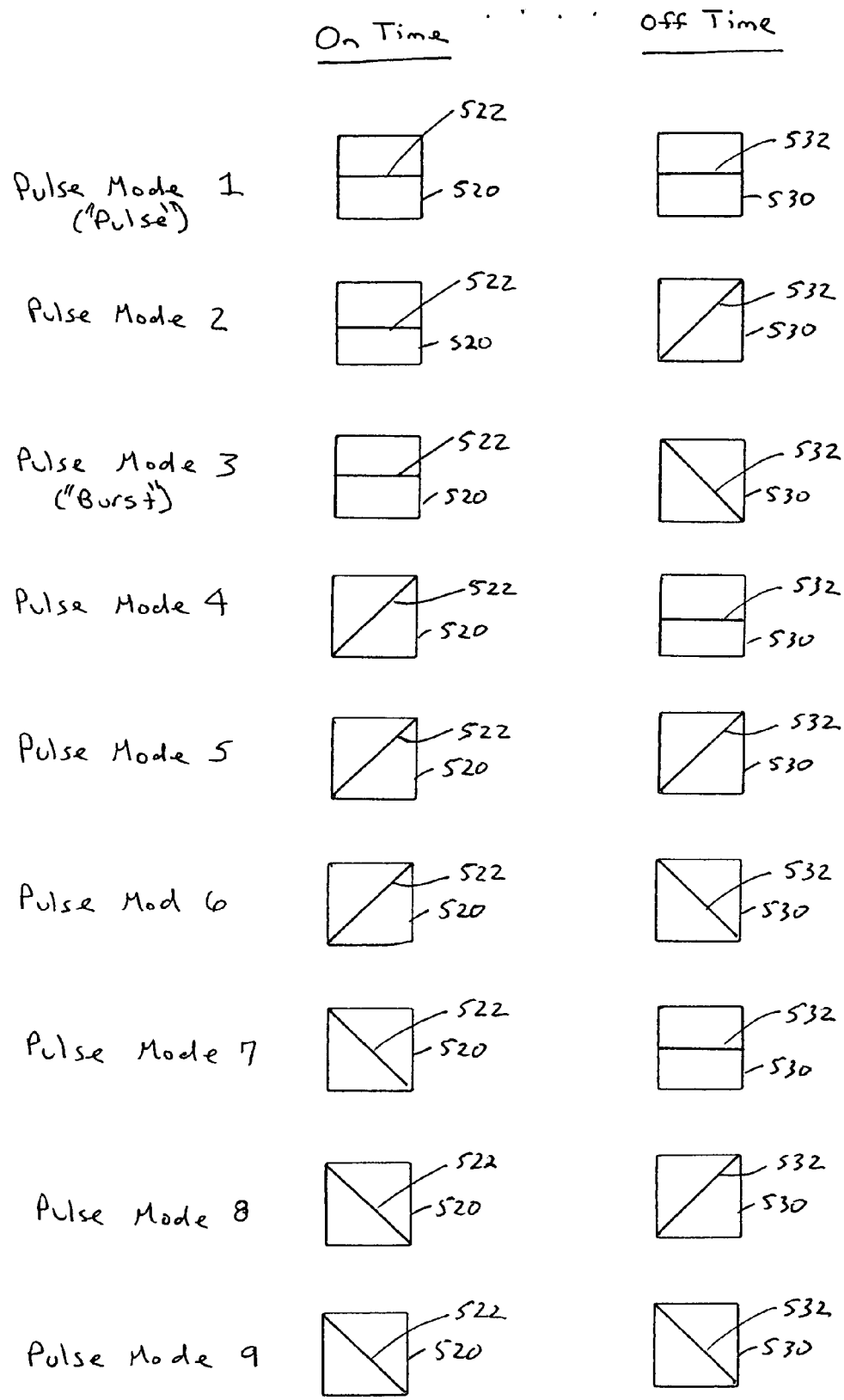
FIG. 11 illustrates nine different pulse modes that can be implemented by selecting one of three on-time representations and one of three off-time representations according to one embodiment.

According to one embodiment, the on-time and the off-time can each be assigned three different representations: linear increasing, linear horizontal or constant, and linear decreasing. Referring to FIG. 11, the total number of possible modes can be determined by multiplying the number of on-time representations and the number of off-time representations. In this embodiment, a surgeon can program nine different pulse modes. Indeed, the number of modes can change when using different numbers of representations.

In Mode 1, both the on-time and the off-time remain substantially constant when the foot pedal is pressed due to the horizontal representations. In Mode 2, the on-time remains substantially constant and the off-time increases linearly in response to the foot pedal being pressed. In Mode 3, the off-time remains substantially constant and the off-time decreases linearly in response to pressing the foot pedal. In Mode 4, the on-time increases linearly and the off-time remains substantially constant in response to pressing the foot pedal. In Mode 5, both the on-time and the off-time increase linearly as the foot pedal is pressed. In Mode 6, the on-time increases linearly and the off-time decreases linearly in response to the foot pedal being pressed. In Mode 7, the on-time decreases linearly and the off-time remains substantially constant in response to pressing the foot pedal. In Mode 8, the on-time decreases linearly and the off-time increases linearly in response to the foot pedal being pressed. In Mode 9, both the on-time and the off-time decrease linearly as the foot pedal is pressed. A surgeon can select one of the nine modes depending on the particular application according to one embodiment. FIGS. 12-19 illustrate exemplary implementations of selected modes. Persons skilled in the art will appreciate that the values provided in FIGS. 12-19 are exemplary values. Indeed, other power, on-time and off-time values may be used as necessary. Accordingly, the values are provided for purposes of explanation, not limitation.

Figure 3:
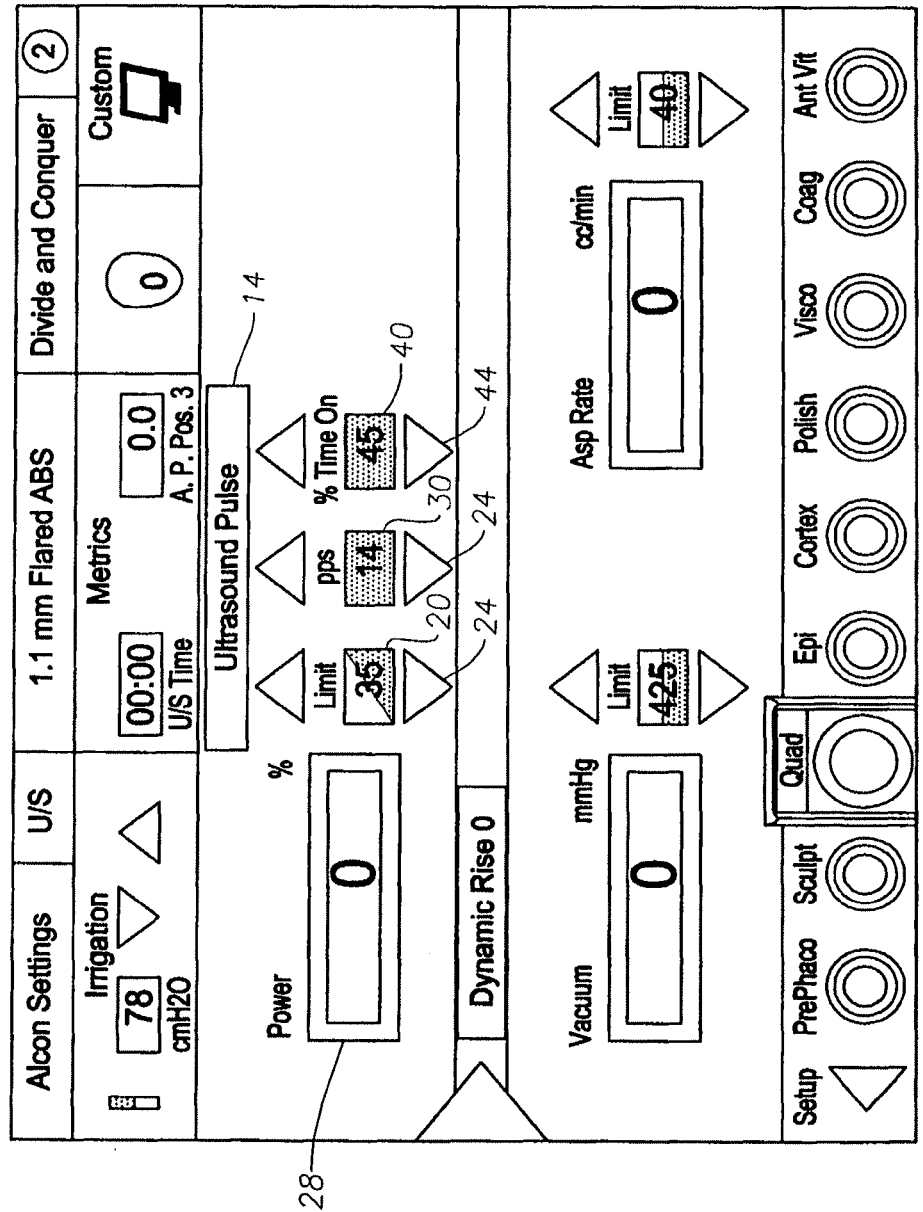
FIG. 3 illustrates the interface shown in FIG. 2 after the "Ultrasound Pulse" menu bar is selected from the menu.
Figure 4:
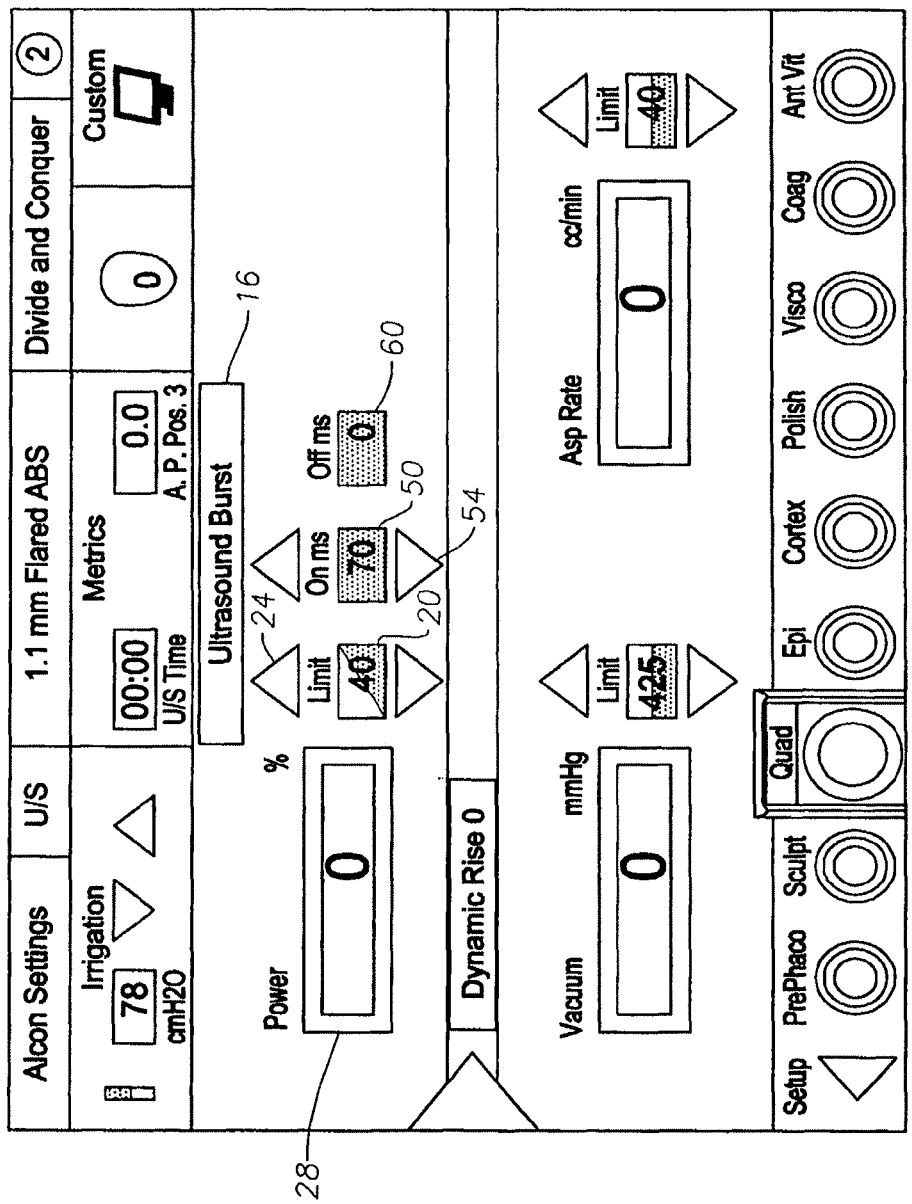
FIG. 4 illustrates the interface shown in FIG. 2 after the "Ultrasound Burst" menu bar is selected from the menu.
Figure 12:
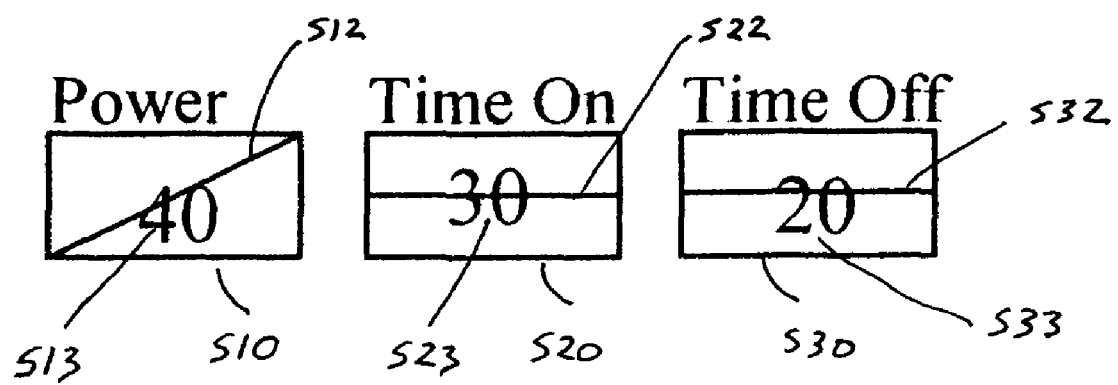
FIG. 12 illustrates an interface according to one embodiment that is set for "pulse" mode by selecting a constant on-time and a constant off-time.

FIG. 12 illustrates an exemplary implementation of Mode 1, which is commonly referred to as "Pulse" mode. In "Pulse" mode, phacoemulsification power is provided in periodic pulses at a constant duty cycle. The surgeon can increase or decrease the amount of power by pressing or releasing the foot pedal, which increases or decreases the amplitude of the fixed-width pulses. In known interfaces, such as the interface shown in FIG. 3, "Pulse" mode is typically set using the pulse rate expressed in pulses per second (pps) and the duty cycle or on-time, which is expressed in % time on. Embodiments of the invention use on-time and off-time to represent pulses in "Pulse" mode. In the illustrated example, power increases from an initial or minimum value to a maximum value of 40% as the foot pedal is depressed. The on-time remains fixed at 30 ms and the off-time remains fixed at 20 ms throughout different foot pedal positions. Thus, power is adjusted by adjusting the amplitude of fixed-width or constant duty cycle pulses.

Figure 13:
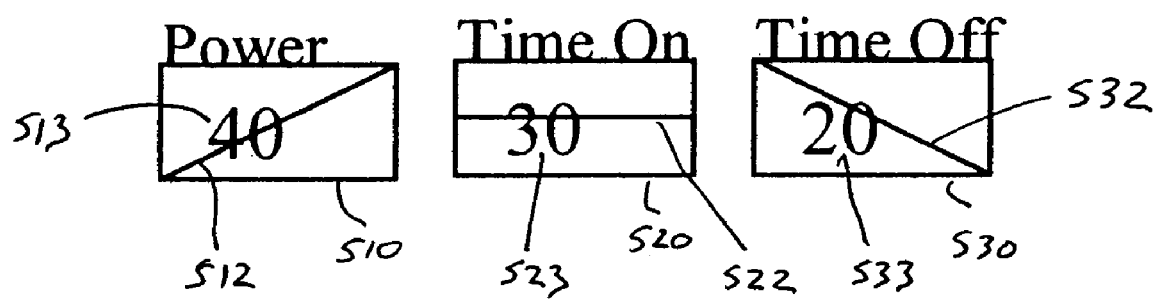
FIG. 13 illustrates an interface according to one embodiment that is set for a "burst" mode by selecting a constant on-time and a decreasing off-time relative to foot pedal displacement.

FIG. 13 illustrates an exemplary implementation of Mode 3, which is commonly referred to as "Burst" mode. In "Burst" mode, power is provided through a series of periodic, constant amplitude pulses. Each pulse is followed by an "off" time. The off-time is varied by pressing the foot pedal to adjust the amount of power that is delivered to the handpiece. In an alternative burst mode, the amplitude of the pulses may also increase. In the illustrated example, the power increases linearly from an initial or minimum value to a maximum value of 40%. The on-time is fixed or constant throughout different foot pedal positions, and the off-time decreases linearly from an initial or maximum value to a minimum value of 20 ms. For Burst mode, the initial value can be programmed or set to 2500 ms. Indeed, other initial values can also be used depending on the particular application.

Figure 14:
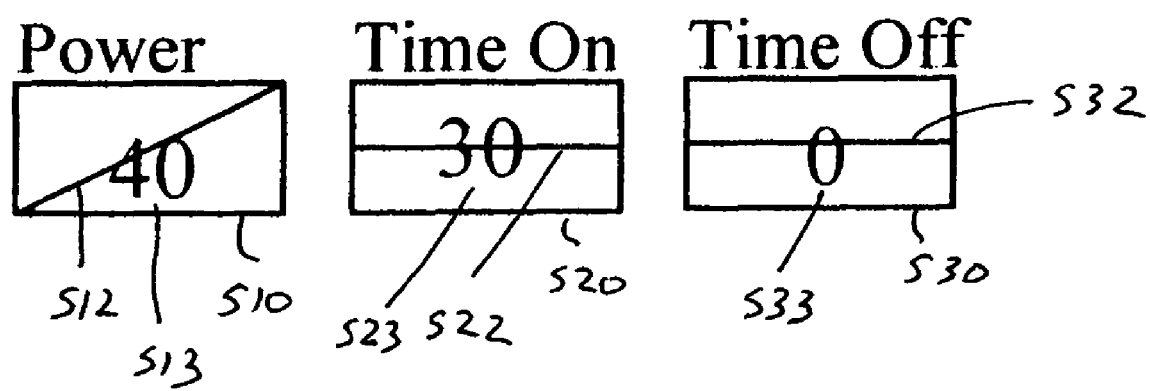
FIG. 14 illustrates an interface according to one embodiment that is set for "continuous" mode in which the off-time is set to zero.

FIG. 14 illustrates an exemplary implementation of "Continuous" mode. A continuous mode can be selected by setting the off-time to zero when in "Pulse" mode (FIG. 12) or other modes besides "Burst" mode (FIG. 13). Ultrasound power is applied continuously in "Continuous" mode and in a linear manner so that the power increases linearly from zero to 40 as the foot pedal is pressed.

Figure 15:
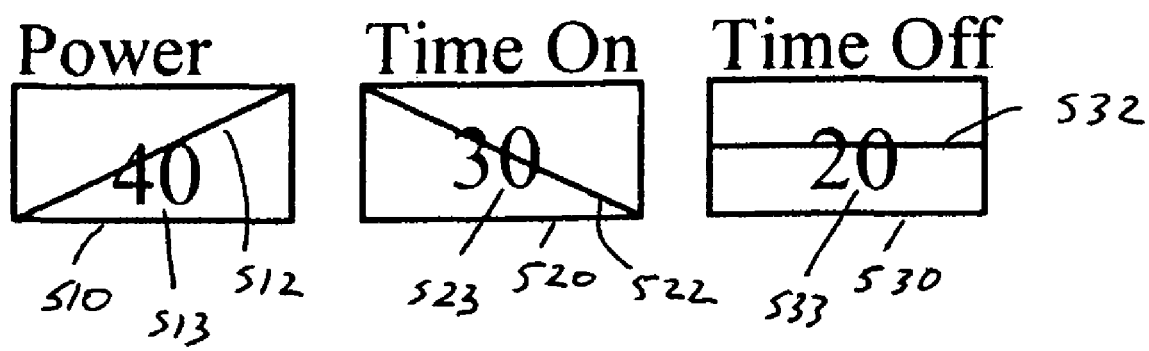
FIG. 15 illustrates an interface according to one embodiment that is set for a mode in which on-time decreases and the off-time remains constant relative to foot pedal displacement.

FIG. 15 illustrates a mode in which the on-time decreases linearly and the off-time remains constant as the foot pedal is pressed. More particularly, this combination results in power increasing linearly from an initial or minimum value to a maximum value of 40%. The on-time decreases linearly from an initial or maximum value, such as 150 ms to a minimum or ending value of 30 ms in a linear manner. The initial value can be, for example, about a factor of five times the ending value. Thus, in this example, the initial value of 150 ms is five times the ending value of 30 ms. The off-time remains fixed at 20 ms throughout different foot pedal positions.

The mode generated by the settings shown in FIG. 15 can be beneficial since the pulses that are generated by the system can be "adaptive" to various lens hardnesses. For example, when the surgeon sees that a given foot pedal depression does not result in sufficiently rapid progress in lens removal, the surgeon will typically command deeper foot pedal penetration, thus resulting in greater power. Usually, greater power will result in increased repulsion, however, repulsion can be reduced, minimized or eliminated since the duration of the ultrasound pulse with this particular setting will be shortened. This result can be particularly useful when a surgeon is attempting to extract extremely mature cataracts, which are more prone to repulsion at higher powers due to their hardness.

Figure 16:
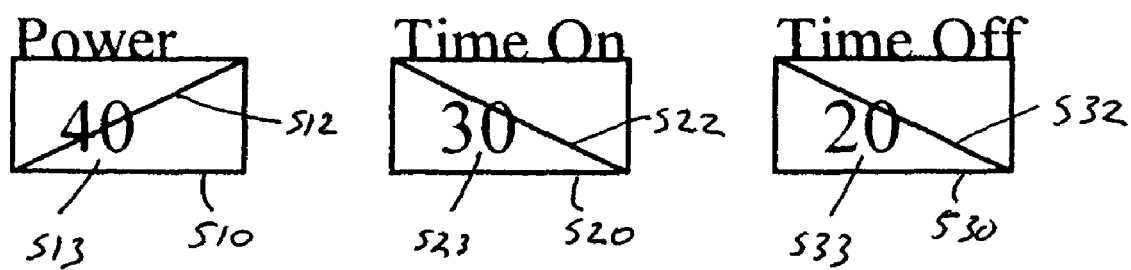
FIG. 16 illustrates an interface according to one embodiment that is set for a mode in which both the on-time and the off-time decrease relative to foot pedal displacement.

FIG. 16 illustrates a mode in which the power of pulses increases linearly from an initial or minimum value to a maximum value of 40%. The on-time decreases linearly from an initial or maximum value to a minimum or ending value of 30 ms. As previously discussed, the initial or maximum value can be about a factor of five times the ending value. Thus, in this example, the initial or maximum value can be 150 ms. The off-time decreases linearly from an initial or maximum value, such as 2500 ms, to a minimum or ending value of 20 ms.

Figure 17:
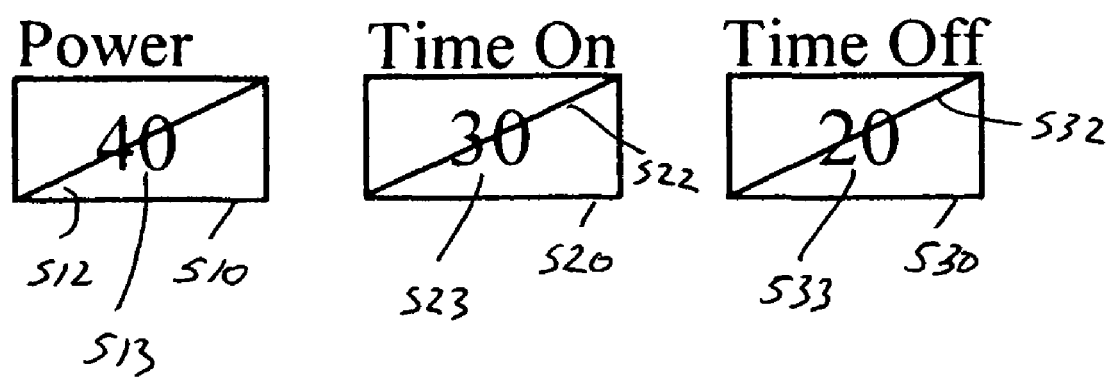
FIG. 17 illustrates an interface according to one embodiment that is set for a mode in which both the on-time and the off-time increase relative to foot pedal displacement.

FIG. 17 illustrates a mode in which the power, on-time and off-time all increase linearly as the foot pedal is pressed. In the illustrated example, the power increases linearly from an initial or minimum value to a maximum or ending value of 40%. The on-time increases linearly from an initial or minimum value, e.g., 6 ms to 20 ms, to a maximum or ending value of 30 ms. The off-time increases linearly from an initial or minimum value, e.g. 4 ms, to a maximum or ending value of 20 ms.

Figure 18:
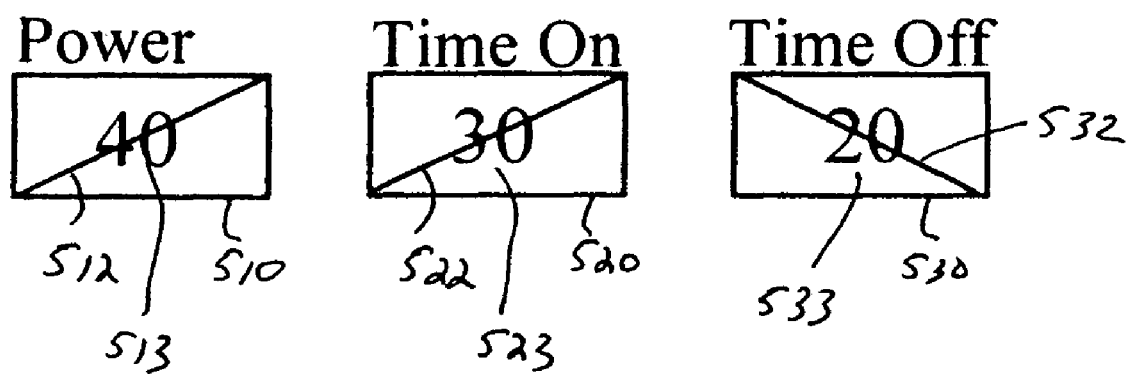
FIG. 18 illustrates an interface according to one embodiment that is set for a mode in which the on-time increases and the off-time decreases relative to foot pedal displacement.

FIG. 18 illustrates a mode in which the power and on-time increase linearly and the off-time decreases linearly. The power increases linearly from an initial or minimum value to a maximum or ending value of 40%. The on-time increases linearly from an initial or minimum value, e.g., 6 ms, to a maximum or ending value of 30 ms. The off-time decreases linearly from an initial or maximum value, e.g., 2500 ms, to a minimum or ending value of 20 ms. Another exemplary implementation of this mode is shown in FIG. 5.

Figure 19:
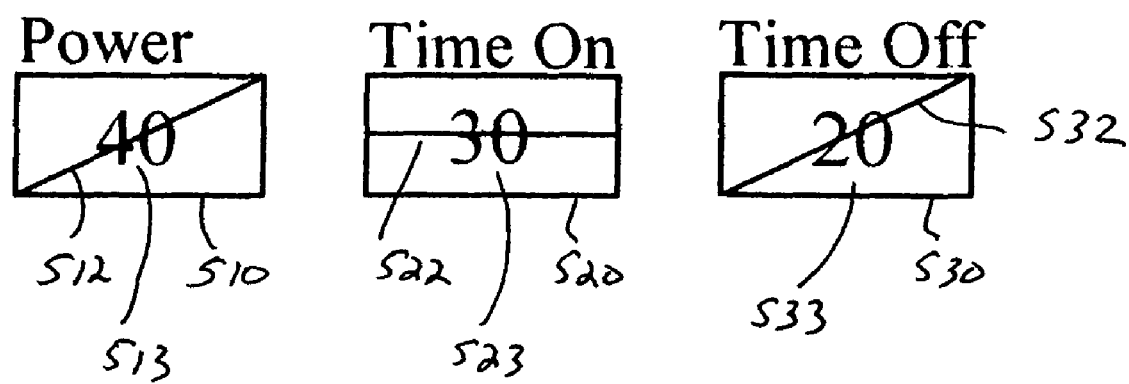
FIG. 19 illustrates an interface according to one embodiment that is set for a mode in which the on-time remains constant and the off-time increases relative to foot pedal displacement.

FIG. 19 illustrates a mode in which the power increases linearly from an initial or minimum value to a maximum or ending value of 40%. The on-time remains constant at 30 ms throughout different foot pedal positions. The off-time increases linearly from an initial or minimum value, e.g., 4 ms, to a maximum or ending value of 20 ms as the foot pedal is pressed.

Figure 20:
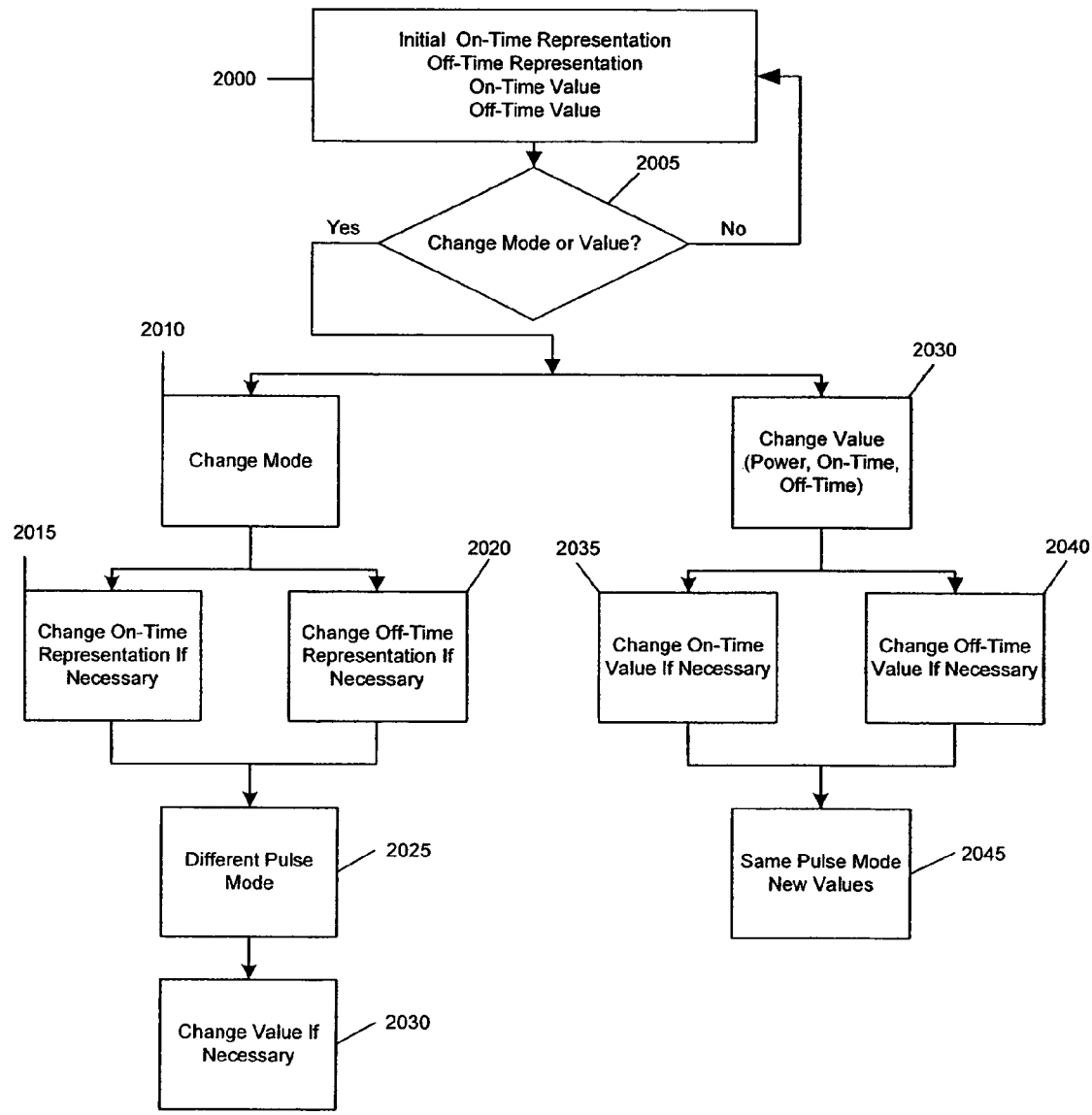
FIG. 20 is a flow chart illustrating a method for selecting a mode and related on-time and off-time values according to one embodiment.

FIG. 20 illustrates a method in which representations and on-time and off-time values can be adjusted. In step 2000, the phacoemulsification surgery system is configured to have an initial on-time representation, an initial off-time representation, an initial on-time value, and an initial off-time value. In step 2005, a decision is made whether the pulse mode or a value of a pulse parameter are to be changed. If not, the initial settings are maintained.

If the pulse mode is to be changed, in step 2010, then the on-time and off-time representations are changed as necessary in steps 2015 and 2020. For example, the surgeon can touch the display screen at an on-time display element to change the on-time representation to one of an increasing linear, constant or decreasing linear representation. Similarly, the surgeon can touch the display screen at an off-time display element to change the off-time representation to one of an increasing linear, constant or decreasing linear representation. The selected combination of the on-time and off-time functions results in one of pulse modes shown in FIG. 11 being selected in step 2025. Of course, different numbers of representations can allow a surgeon to generate different number of pulse modes.

The values of the on-time and off-time parameters can be adjusted in step 2030. More specifically, the on-time value and the off-time value can be adjusted as necessary in steps 2035 and 2040. Thus, the values of the pulse mode are adjusted in step 2045 as necessary.

FIGS. 21-25 illustrate an alternative embodiment of the invention in which a window can be generated in response to touching the display screen to enable a user to change pulse modes, adjust the value of a parameter and/or the function or representation of the parameter. The embodiment shown in FIGS. 21-25 can be used separately from or in conjunction with the embodiments described and shown in FIGS. 5-19.

Figure 21:
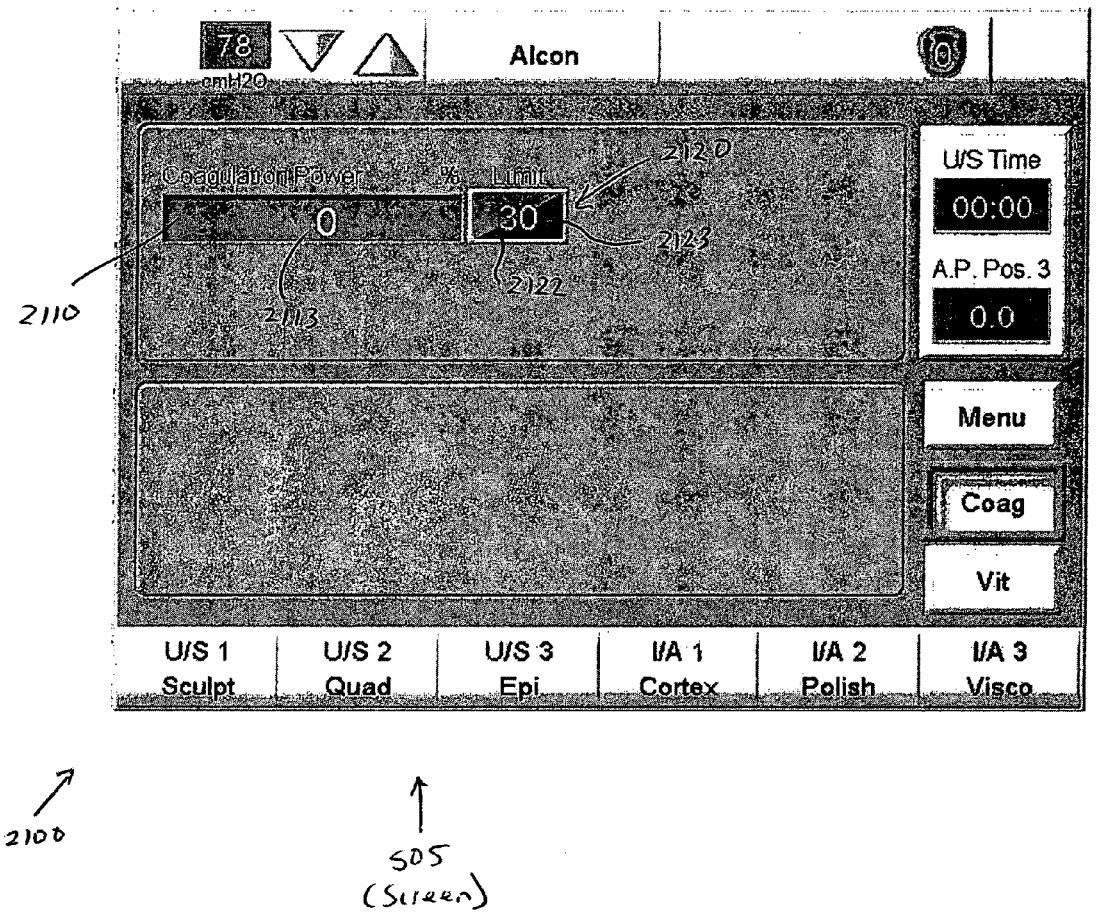
FIG. 21 illustrates an interface screen for use with a phacoemulsification surgical system that shows a continuous surgical parameter value and a representation of the function of the parameter.

Referring to FIG. 21, an exemplary user interface screen 2100 includes a field 2110 and a display element 2120. The display element 2120 includes a representation 2122 of, for example, a non-ultrasound parameter such as coagulation power, and a maximum or minimum value or limit 2123 of the parameter. In the illustrated embodiment, the value is a maximum value since the representation indicates that the power increases as a foot pedal is pressed or another controller is actuated. The current value 2113 of the parameter, expressed as a percentage of the limit 2123, is indicated in the field 2110.

The display element 2120 includes a representation 2123 of the behavior or function of the parameter relative to a position of a controller, such as the foot pedal. A representation 2122 of a parameter can have various shapes depending on the desired relationship or function between the parameter and the position of the foot pedal. For example, the representation 2122 can be linear or non-linear (e.g., exponential or polynomial). The display element 2120 is similar to the display element describe above and shown in FIGS. 5-19. Accordingly, additional details concerning the display element 2120 are not repeated. Further, for purposes of explanation and illustration, not limitation, this specification refers to linear representations, e.g., increasing linear, constant, and decreasing linear representations and related linear functions of power. Persons skilled in the art will appreciate that other parameters, such as on-time and off-time, can be controlled, and that parameters can be controlled with linear representations, non-linear representations and combinations thereof.

Figure 22:
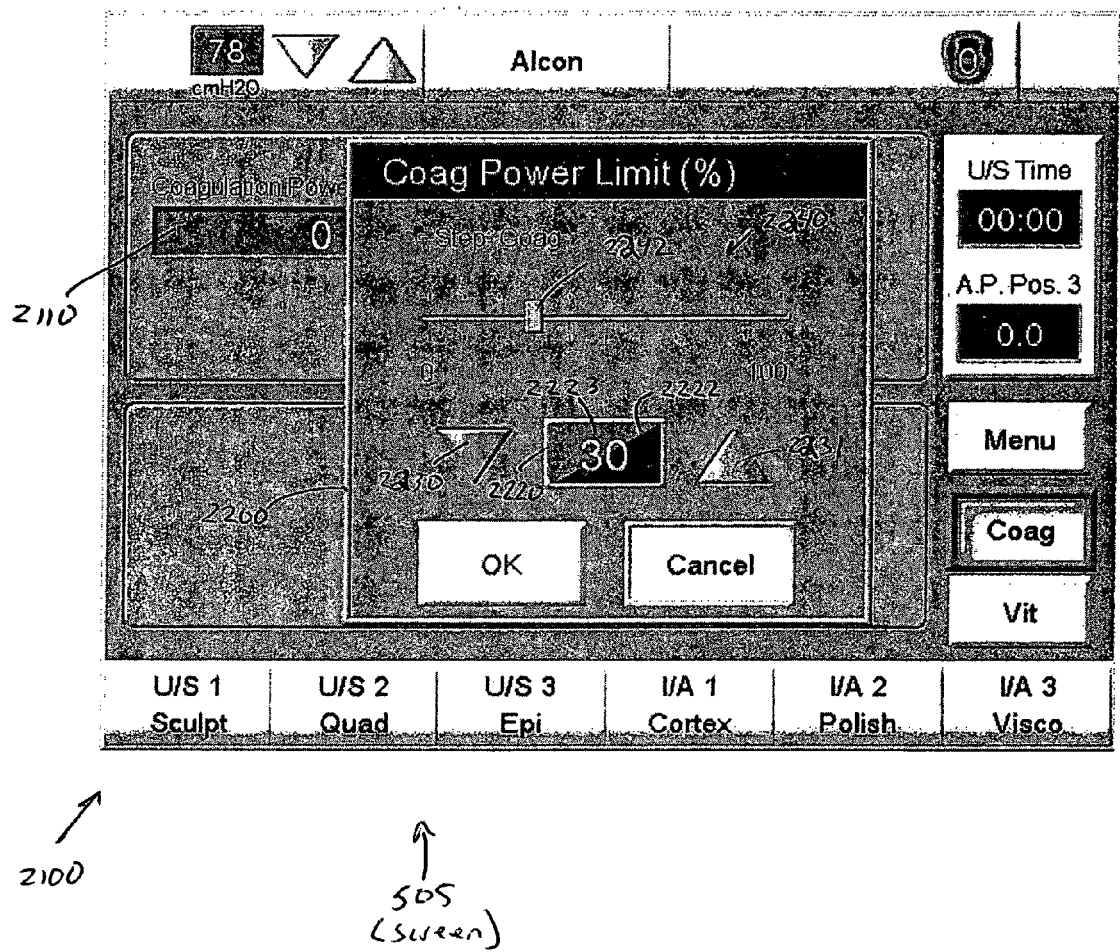
FIG. 22 illustrates an alternative embodiment of the invention in which a separate display window is generated on the display screen of a phacoemulsification system in response to touching the screen.

Referring to FIG. 22, according to one embodiment a window 2200 is displayed over the initial display screen 2100 in response to a user touching the display screen, e.g., at or around the display element 2120. The window 2200 includes a display element 2220 having a representation 2222, which is the same as the representation 2122 of the display element 2122 on the initial display screen 2100 behind the window 2200. The window 2200 also includes a maximum value or limit 2223, which is the same as the value 2123 in the display screen 2100 behind the window 2100. The window 2200 can be various shapes and sizes. In the illustrated embodiment, the window 2200 is square and covers a portion of the initial display 2100.

The window 2200 also includes one or more adjustment elements, such as arrows, e.g., up/down arrows 2230 and 2231 (generally 2230) and a slide bar 2240. The window 2200 can include one arrow, multiple arrows, a slide bar and a combination thereof.

Figure 23:
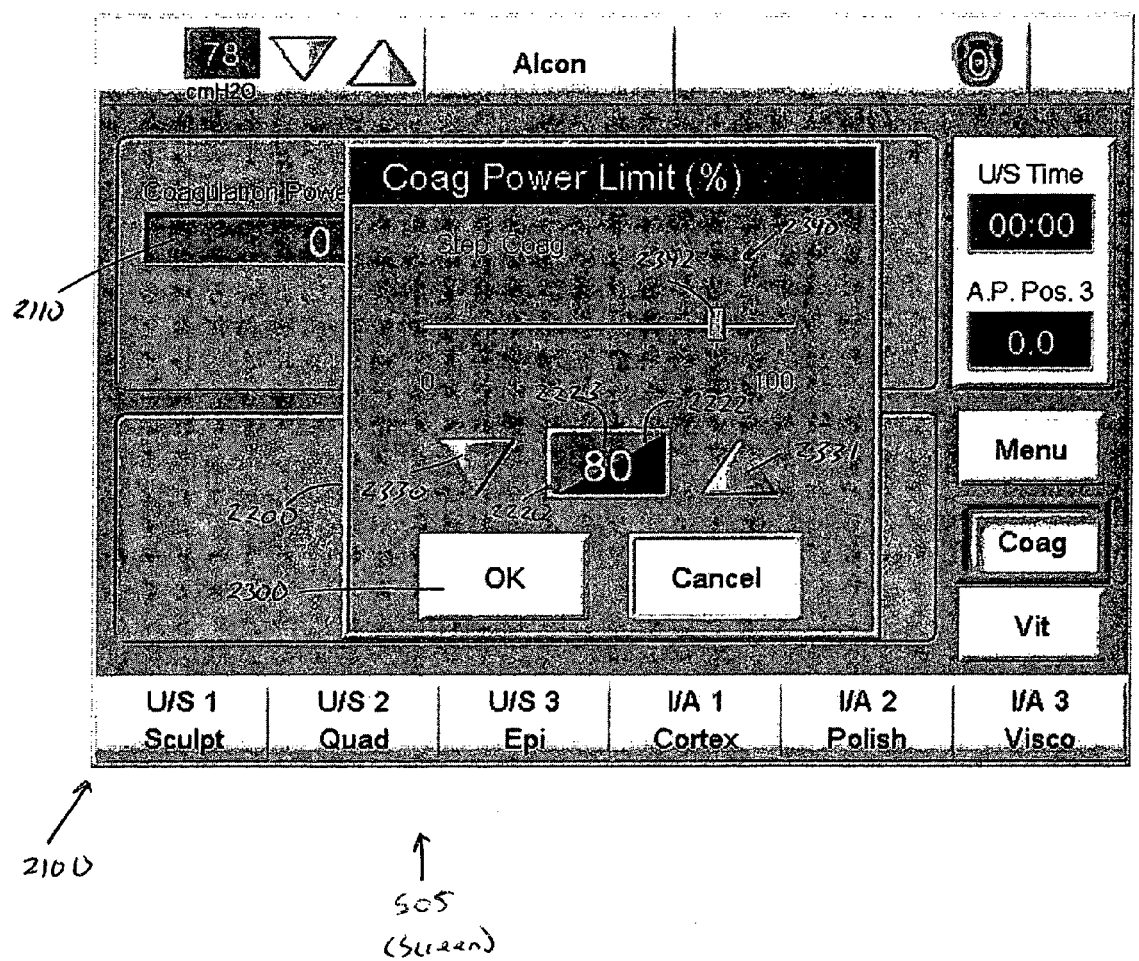
FIG. 23 illustrates adjusting a value of a parameter using an arrow or a slide bar in the window.
Figure 24:
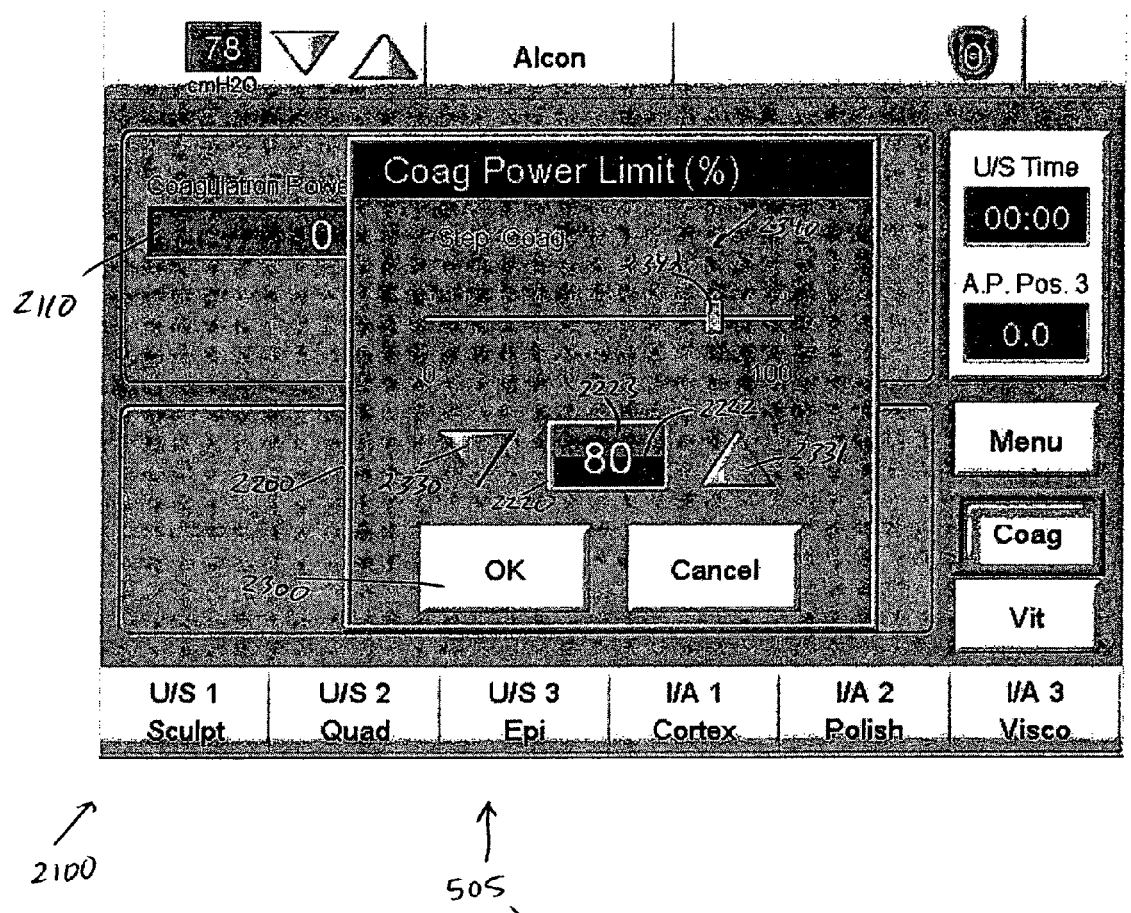
FIG. 24 illustrates adjusting a representation of the function of the parameter by touching the window.

Referring to FIG. 23, a user can touch an arrow 2230 or move a marker 2242 of the slide bar 2240 to adjust the value up or down. For example, as shown in FIGS. 22 and 23, the value is adjusted from 30 to 80 by pressing the up arrow 2231 or moving the marker 2242 to the right. Referring to FIG. 24, the representation of the function of the parameter can also be adjusted by touching the display screen 505 at the display element 2220 in the window 2000. Touching the display element 2220 in the window 2000 changes a current representation of the parameter to a different representation. For example, as shown in FIG. 10, a user can scroll through the different available representations by touching the display element 2200 in the window 2000. Alternatively, a menu can be displayed, e.g., as shown in FIG. 9.

Referring to FIGS. 23 and 24, after the representation and/or value of the parameter has been adjusted, the window 2000 can be closed touching the display screen at a pre-defined area 2300 of the window. For example, in the illustrated embodiment, the pre-defined area 2300 can be an "OK" box or button or another area in the window 2000.

Figure 25:
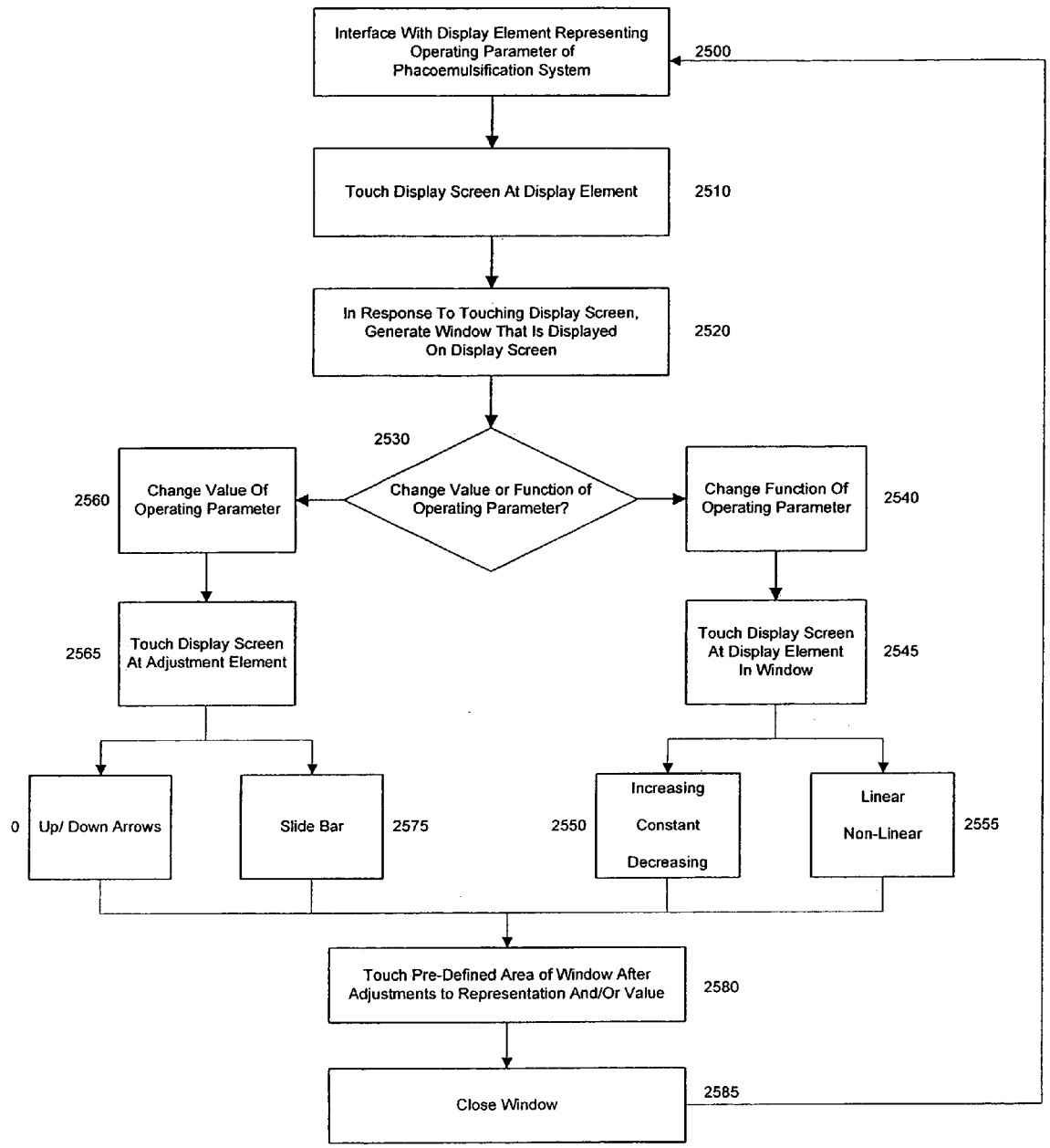
FIG. 25 is a flow chart illustrating a method for adjusting a parameter of a phacoemulsification system by generating a separate display window that is displayed on the display screen.

FIG. 25 illustrates a method of adjusting values and representations of parameters according to one embodiment. In step 2500, an interface or interface screen is generated. The interface includes a display element that represents a parameter, such as on-time and off-time (or a non-ultrasound parameter) of the phacoemulsification surgery system. In step 2510, a user touches the screen of the display, e.g., at a display element or another pre-defined area. In step 2520, a window is generated in response to touching the display screen. The window enables the user to adjust the representation of the function of the parameter or the value of the parameter in step 2530.

Steps 2540-2555 illustrate changing a representation of the function of the parameter. In step 2545, the user touches the display screen at the display element to adjust the representation. The adjustment can be to make the representation increasing, constant or decreasing in step 2550 and/or to change the representation to linear or non-linear.

Steps 2560-2575 illustrate changing a value of the parameter. In step 2565, the user touches the display screen at the display element to adjust the value. The adjustment can be made using arrows, such as up/down arrows in step 2570 and/or using a slide bar in step 2575. If both the representation and limit value are to be adjusted, the representation can be adjusted first, and then the value. Alternatively, the limit value can be adjusted first and then the representation.

In step 2580, after the representation and/or value of the parameter has been adjusted, the window can be closed touching the display screen at a pre-defined area of the window. In step 2585, the window is closed and the interface includes an updated display element. Further adjustments can be made in a similar manner if necessary.

Persons skilled in the art will recognize that the graphical user interface and adjustments to the on-time and the off-time can be modified in various ways. Accordingly, persons skilled in the art will appreciate that embodiments are not limited to the particular exemplary embodiments described, but rather, embodiments can be applied to other surgical equipment and parameters. For example, embodiments can be used with other surgical devices, such as coagulation forceps and vitrectomy probes. Although references have been made in the foregoing description to various embodiments, persons skilled in the art will recognize that insubstantial modifications, alterations, and substitutions can be made to the described embodiments without departing from the invention as recited in the accompanying claims.

We claim:

1. A user interface for a phacoemulsification surgical system that generates pulses having an on-time and an off-time, the pulses being adjusted in response to a controller based on settings displayed on a display screen, the user interface comprising:

a first display element that includes a representation of the on-time relative to a position of the controller, wherein the on-time representation is changed to a different on-time representation in response to touching the display screen at the first display element; and a second display element that includes a representation of the off-time relative to a position of the controller, wherein the off-time representation is changed to a different off-time representation in response to touching the display screen at the second display element, the on-time and off-time representations being selected to generate pulses in a desired mode.

2. The user interface of claim 1, wherein at least three different on-time representations are sequentially displayed in the first display element by touching the display screen at the first display element to scroll through the at least three on-time representations.

3. The user interface of claim 2, wherein the on-time representation is replaced by a different on-time representation each time the display screen is touched.

4. The user interface of claim 1, wherein the on-time representation is linear.

5. The user interface of claim 4, wherein the controller is a foot pedal and the linear on-time representation is an increasing linear on-time representation that represents the on-time increasing linearly in response to movement of the foot pedal.

6. The user interface of claim 4, wherein the controller is a foot pedal and the linear on-time representation is a horizontal linear on-time representation that represents the on-time remaining substantially constant regardless of movement of the foot pedal.

7. The user interface of claim 4, wherein the controller is a foot pedal and the linear on-time representation is a decreasing linear on-time representation that represents the on-time decreasing linearly in response to movement of the foot pedal.

8. The user interface of claim 1, further comprising an adjustment element that is displayed on the display screen and associated with the on-time, wherein an on-time value is adjusted by touching the display screen at the adjustment element.

9. The user interface of claim 1, further comprising an on-time value display within the first display element that indicates an on-time value.

10. The user interface of claim 1, wherein at least three on-time representations are presented in a menu that is displayed on the display screen in response to touching the display screen at the first display element.

11. The user interface of claim 1, wherein the on-time representation is non-linear.

12. The user interface of claim 11, wherein the non-linear on-time representation is an exponential or a polynomial.

13. The user interface of claim 1, wherein at least three different off-time representations are sequentially displayed in the second display element by touching the display screen at the second display element to scroll through the at least three off-time representations.

14. The user interface of claim 13, wherein the current off-time representation is replaced by a different off-time representation each time the display screen is touched.

15. The user interface of claim 1, wherein the off-time representation is linear.

16. The user interface of claim 15, wherein the controller is a foot pedal and the linear off-time representation is an increasing linear off-time representation that represents the off-time increasing linearly in response to movement of the foot pedal.

17. The user interface of claim 15, wherein the controller is a foot pedal and the linear off-time representation is a horizontal linear off-time representation that represents the off-time remaining substantially constant regardless of movement of the foot pedal.

18. The user interface of claim 15, wherein the controller is a foot pedal and the linear off-time representation is a decreasing linear off-time representation that represents the off-time decreasing linearly in response to movement of the foot pedal.

19. The user interface of claim 1, further comprising an adjustment element that is displayed on the display screen and associated with the off-time, wherein an off-time value is adjusted by touching the display screen at the adjustment element.

20. The user interface of claim 1, further comprising an off-time value display within the second display element that indicates an off-time value.

21. The user interface of claim 1, wherein at least three off-time representations are presented in a menu that is displayed on the display screen in response to touching the display screen at the second display element.

22. The user interface of claim 1, wherein the off-time representation is non-linear.

23. The user interface of claim 22, wherein the non-linear off-time representation is an exponential or a polynomial.

24. The user interface of claim 1, wherein a total number of available pulse modes is calculated by multiplying the number of on-time representations and the number of off-time representations.

25. The user interface of claim 24, wherein nine pulse modes can be selected with three on-time representations and three off-time representations.

26. The user interface of claim 1, wherein the phacoemulsification surgical system generates pulse mode pulses when the on-time representation in the first display element is a horizontal linear representation that represents the on-time remaining substantially constant, and the off-time representation in the second display element is a horizontal linear representation that represents the off-time remaining substantially constant.

27. The user interface of claim 1, wherein the phacoemulsification surgical system generates burst mode pulses when the on-time representation in the first display element is a horizontal linear representation that represents the on-time remaining substantially constant, and the off-time representation in the second display element is a decreasing linear representation that represents the off-time decreasing linearly in response to movement of the controller.

28. The user interface of claim 1, wherein the current off-time representation is changed using a menu.

29. The user interface of claim 1, wherein the current on-time representation is changed using a menu.

30. A user interface for a phacoemulsification surgical system that generates pulses having an on-time and an off-time, the pulses being adjusted in response to a controller based on settings displayed on a display screen, wherein the controller is a foot pedal, the user interface comprising:

a first display element that includes a selected representation of the on-time relative to a position of the foot pedal, wherein at least three on-time representations are sequentially displayed in the first display element by touching the display screen at the first display element to scroll through the at least three on-time representations, the on-time representation that is displayed in the first display element being the selected on-time representation; and a second display element that includes a selected representation of the off-time relative to a position of the foot pedal, wherein at least three off-time representations are sequentially displayed in the second display element by touching the display screen at the second display element to scroll through the at least three off-time representations, the off-time representation that is displayed in the second display element being the selected off-time representation, the on-time and off-time representations being selected to generate pulses in a desired mode.

31. The user interface of claim 30, wherein the current on-time representation is replaced by a different on-time representation each time the display screen is touched.

32. The user interface of claim 30, wherein the on-time representation is linear.

33. The user interface of claim 30, further comprising an on-time value display within the first display element that indicates an on-time value.

34. The user interface of claim 30, wherein the on-time representation is non-linear.

35. The user interface of claim 34, wherein the non-linear on-time representation is an exponential or a polynomial.

36. The user interface of claim 30, wherein the current off-time representation is replaced by a different off-time representation each time the display screen is touched.

37. The user interface of claim 30, wherein the off-time representation is linear.

38. The user interface of claim 30, further comprising an off-time value display within the second display element that indicates an off-time value.

39. The user interface of claim 30, wherein the off-time representation is non-linear.

40. The user interface of claim 39, wherein the non-linear off-time representation is an exponential or a polynomial.

41. The user interface of claim 30, wherein nine pulse modes can be selected with three on-time representations and three off-time representations.

42. A user interface for a phacoemulsification surgical system that generates pulses having an on-time and an off-time, the pulses being adjusted in response to a foot pedal and based on settings in a user interface displayed on a display screen, the user interface comprising:

a first display element that includes a selected representation of the on-time of pulses generated by the phacoemulsification system relative to a position of the foot pedal, wherein the on-time representation is a decreasing linear or non-linear representation, a horizontal representation, or an increasing linear or non-linear representation, wherein at least three on-time representations are sequentially displayed in the first display element by touching the display screen at the first display element to scroll through the at least three on-time representations, the on-time representation that is displayed in the first display element being the selected on-time representation;

an on-time value that is displayed with the first display element and that indicates a value of the on-time of the pulses, wherein the on-time representation is displayed in the background relative to the on-time value;

a second display element that includes a selected representation of the off-time of pulses generated by the phacoemulsification system relative to a position of the foot pedal, wherein the off-time representation is a decreasing linear or non-linear representation, a horizontal representation, or an increasing linear or non-linear representation, wherein at least three off-time representations are sequentially displayed in the second display element by touching the display screen at the second display element to scroll through the at least three off-time representations, the off-time representation that is displayed in the second display element being the selected off-time representation; and an off-time value display that indicates a value of the off-time of the pulses, wherein the off-time value display appears within the second display element and the off-time representation is displayed in the background relative to the off-time value, the on-time and off-time representations being selected to generate pulses in a desired mode.

43. The user interface of claim 42, wherein the current on-time representation is replaced by a different on-time representation each time the display screen is touched.

44. The user interface of claim 42, wherein the non-linear on-time representation is an exponential or a polynomial.

45. The user interface of claim 42, wherein the current off-time representation is replaced by a different off-time representation each time the display screen is touched.

46. The user interface of claim 42, wherein the non-linear off-time representation is an exponential or a polynomial.

47. The user interface of claim 42, wherein nine pulse modes can be selected with three on-time representations and three off-time representations.

\* \* \* \* \*